(12) United States Patent
Haji Reza et al.

(10) Patent No.: US 12,207,902 B2
(45) Date of Patent: Jan. 28, 2025

(54) PHOTOACOUSTIC REMOTE SENSING (PARS)

(71) Applicant: ILLUMISONICS INC., Waterloo (CA)

(72) Inventors: Parsin Haji Reza, Waterloo (CA); Roger Zemp, Waterloo (CA)

(73) Assignee: ILLUMISONICS INC., Waterloo (CA)

(*) Notice: Subject to any disclaimer, the term of this patent is extended or adjusted under 35 U.S.C. 154(b) by 251 days.

(21) Appl. No.: 17/693,690

(22) Filed: Mar. 14, 2022

(65) Prior Publication Data

US 2022/0265148 A1 Aug. 25, 2022

Related U.S. Application Data

(63) Continuation of application No. 16/847,182, filed on Apr. 13, 2020, now Pat. No. 11,298,027, which is a (Continued)

(51) Int. Cl.
*A61B 5/00* (2006.01)
*G01N 21/17* (2006.01)

(52) U.S. Cl.
CPC ....... *A61B 5/0095* (2013.01); *G01N 21/1702* (2013.01); *G01N 21/1717* (2013.01); (Continued)

(58) Field of Classification Search
CPC ............. A61B 5/0095; G01N 21/1702; G01N 21/1717; G01N 2021/1706; (Continued)

(56) References Cited

U.S. PATENT DOCUMENTS 4,710,030 A 12/1987 Tauc et al.
5,070,733 A 12/1991 Nagata et al.
(Continued)

FOREIGN PATENT DOCUMENTS

CN 101526483 A 9/2009
CN 103048271 A 4/2013
(Continued)

OTHER PUBLICATIONS

Hajireza, Parsin, Alexander Forbrich, and Roger J. Zemp. "Multifocus optical-resolution photoacoustic microscopy using stimulated Raman scattering and chromatic aberration." Optics letters 38.15 (2013): 2711-2713. (Year: 2013).*

(Continued)

*Primary Examiner* — Dominic J Bologna
(74) *Attorney, Agent, or Firm* — Bookoff McAndrews, PLLC

(57) ABSTRACT

A photoacoustic remote sensing system (PARS) for imaging a subsurface structure in a sample has an excitation beam configured to generate ultrasonic signals in the sample at an excitation location; an interrogation beam incident on the sample at the excitation location, a portion of the interrogation beam returning from the sample that is indicative of the generated ultrasonic signals; an optical system that focuses at least one of the excitation beam and the interrogation beam with a focal point that is below the surface of the sample; and a detector that detects the returning portion of the interrogation beam.

20 Claims, 26 Drawing Sheets

Related U.S. Application Data continuation of application No. 16/116,038, filed on Aug. 29, 2018, now Pat. No. 10,682,061, which is a continuation of application No. 14/919,565, filed on Oct. 21, 2015, now Pat. No. 10,117,583.

(60) Provisional application No. 62/067,197, filed on Oct. 22, 2014.

(52) U.S. Cl.
CPC ............... *G01N 2021/1706* (2013.01); *G01N 2021/1725* (2013.01); *G01N 2201/06113* (2013.01); *G01N 2201/08* (2013.01); *G01N 2201/0846* (2013.01)

(58) Field of Classification Search
CPC . G01N 2021/1725; G01N 2201/06113; G01N 2201/08; G01N 2201/0846
See application file for complete search history.

(56) References Cited

U.S. PATENT DOCUMENTS

| | | | |
|---|---|---|---|
| 5,479,259 A | 12/1995 | Nakata et al. | |
| 5,615,675 A | 4/1997 | O'Donnell et al. | |
| 5,991,479 A | 11/1999 | Kleinerman | |
| 6,016,202 A | 1/2000 | Fuchs et al. | |
| 6,078,397 A | 6/2000 | Monchalin et al. | |
| 6,256,100 B1 | 7/2001 | Banet et al. | |
| 6,973,830 B2 | 12/2005 | Pepper et al. | |
| 6,992,829 B1 | 1/2006 | Jennings et al. | |
| 7,068,842 B2 | 6/2006 | Liang et al. | |
| 8,004,689 B2 | 8/2011 | Monchalin et al. | |
| 8,180,134 B2 | 5/2012 | Wang | |
| 8,454,512 B2 | 6/2013 | Wang et al. | |
| 8,692,155 B2 | 4/2014 | Bischoff et al. | |
| 9,153,931 B2 | 10/2015 | Ichihara et al. | |
| 9,999,354 B2 | 6/2018 | Rousseau et al. | |
| 10,117,583 B2 * | 11/2018 | Reza ................. | G01N 21/1717 |
| 10,327,646 B2 | 6/2019 | Haji Reza et al. | |
| 10,682,061 B2 * | 6/2020 | Reza ................... | A61B 5/0095 |
| 11,298,027 B2 * | 4/2022 | Haji Reza .......... | G01N 21/1702 |
| 2001/0046049 A1 * | 11/2001 | Aspnes .............. | G01N 21/211 356/369 |
| 2006/0184042 A1 | 8/2006 | Wang et al. | |
| 2006/0262316 A1 | 11/2006 | Baney | |
| 2007/0187632 A1 | 8/2007 | Igarashi | |
| 2008/0123083 A1 | 5/2008 | Wang et al. | |
| 2008/0194929 A1 | 8/2008 | Pesach et al. | |
| 2009/0170149 A1 | 7/2009 | Viator et al. | |
| 2010/0268042 A1 * | 10/2010 | Wang ................. | A61B 5/14546 73/587 |
| 2011/0108707 A1 | 5/2011 | Cui et al. | |
| 2012/0200845 A1 * | 8/2012 | Rousseau ............. | A61B 5/0093 356/72 |
| 2012/0320368 A1 | 12/2012 | Jiao et al. | |
| 2013/0199299 A1 | 8/2013 | Wang et al. | |
| 2014/0118749 A1 | 5/2014 | Nakajima et al. | |
| 2014/0142404 A1 | 5/2014 | Wang et al. | |
| 2014/0185055 A1 | 7/2014 | Wang | |
| 2014/0247456 A1 | 9/2014 | Horstmann et al. | |
| 2015/0077819 A1 | 3/2015 | Schnell et al. | |
| 2015/0148655 A1 | 5/2015 | Haupt et al. | |
| 2015/0150465 A1 | 6/2015 | Irisawa et al. | |
| 2015/0153269 A1 | 6/2015 | Nakatsuka | |
| 2015/0164337 A1 | 6/2015 | Kim et al. | |
| 2015/0185187 A1 | 7/2015 | Wang et al. | |
| 2015/0221081 A1 | 8/2015 | Chang et al. | |
| 2015/0265156 A1 | 9/2015 | Tanaka | |
| 2016/0113507 A1 | 4/2016 | Reza et al. | |
| 2017/0215738 A1 | 8/2017 | Reza et al. | |

FOREIGN PATENT DOCUMENTS

| | | | |
|---|---|---|---|
| CN | 109363639 A | 2/2019 | |
| DE | 10 2010 012 809 A1 | 9/2011 | |
| WO | 2009055705 A2 | 4/2009 | |
| WO | 2009055705 A3 | 6/2009 | |
| WO | WO-2011152747 A1 * | 12/2011 | ........... A61B 5/0095 |
| WO | 2013023210 A1 | 2/2013 | |
| WO | 2013166044 A1 | 11/2013 | |
| WO | 2014027316 A2 | 2/2014 | |
| WO | 2014036405 A2 | 3/2014 | |
| WO | 2014062529 A1 | 4/2014 | |
| WO | 2014160116 A1 | 10/2014 | |
| WO | 2014168930 A1 | 10/2014 | |

OTHER PUBLICATIONS

Beard, Paul. "Biomedical Photoacoustic Imaging." Interface Focus 1.4 (2011): 602-631. PMC. Web. Dec. 12, 2017.

International Search Report and Written Opinion mailed Dec. 19, 2018 in International Application No. PCT/IB2018/057585 (25 pages).

Kevan L. Bell et al., "Coherence-gated photoacoustic remote sensing microscopy", Optics Express, vol. 26, No. 18, Sep. 3, 2018, 16 pp.

Zhihua Ding et al., "Real-time phase-resolved optical coherence tomography and optical Doppler tomography", Optics Express, vol. 10, No. 5, Mar. 11, 2002, 10 pages.

Cedric Blatter et al., "Intrasweep phase-sensitive optical coherence tomography for noncontact optical photoacoustic imaging", Optics Letters, vol. 37, No. 21, Nov. 1, 2012, 4 pp.

Adhikari et al., "Photothermal Microscopy: Imaging the Optical Absorption of Single Nanoparticles and Single Molecules," ACS Nano 2020, 14 (12), 16414-16445 (32 pages).

Tavakolian et al., "Perspective: Principles and specifications of photothermal imaging methodologies and their applications to non-invasive biomedical and non-destructive materials imaging," J. Appl. Phys. 124, 160903 (2018) (13 pages).

* cited by examiner

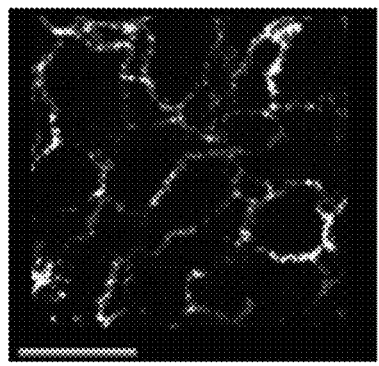 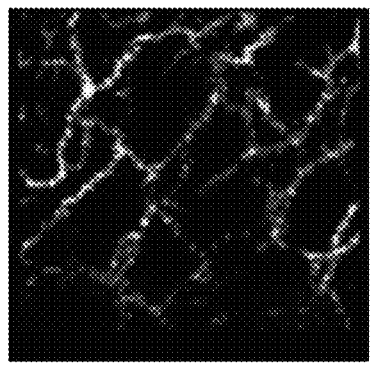 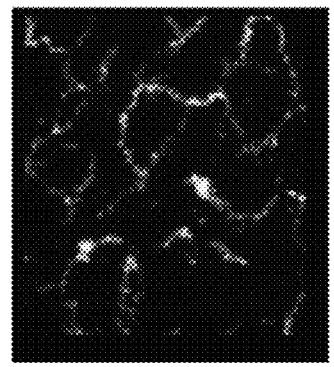
FIG. 23A        FIG. 23B        FIG. 23C
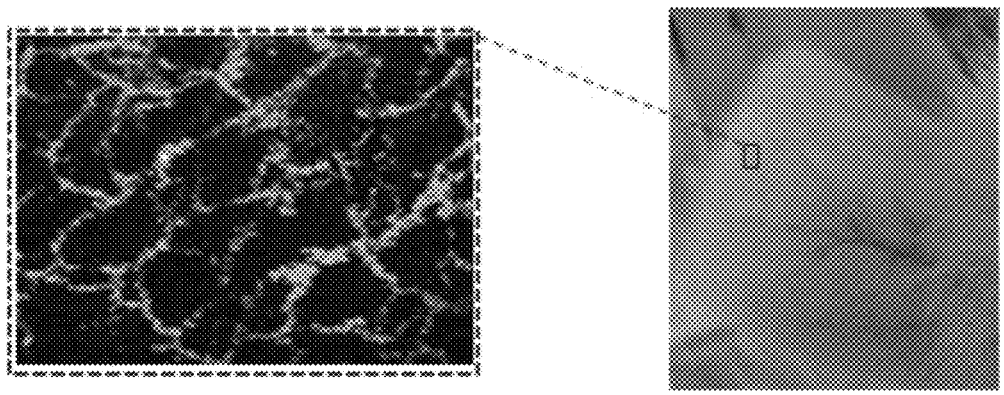
FIG. 24

PHOTOACOUSTIC REMOTE SENSING (PARS)

CROSS-REFERENCE TO RELATED APPLICATION(S)

This patent application is a continuation of U.S. patent application Ser. No. 16/847,182, filed on Apr. 13, 2020, which is a continuation of U.S. patent application Ser. No. 16/116,038, filed on Aug. 29, 2018, now U.S. Pat. No. 10,682,061, which is a continuation of U.S. patent application Ser. No. 14/919,565, filed on Oct. 21, 2015, now U.S. Pat. No. 10,117,583, which claims priority to U.S. Provisional Application No. 62/067,197, filed Oct. 22, 2014, the entireties of which are incorporated herein by reference.

BACKGROUND

Technical Field

This relates to the field of biomedical optics imaging and, in particular, to a laser and ultrasound-based method and system for in vivo or ex vivo, non-contact imaging of biological tissue.

Description of the Related Art

Photoacoustic imaging is an emerging hybrid imaging technology providing optical contrast with high spatial resolution. Nanosecond or picosecond laser pulses fired into tissue launch thermo-elastic-induced acoustic waves which are detected and reconstructed to form high-resolution images. Photoacoustic imaging has been developed into multiple embodiments, including photoacoustic tomography (PAT), photoacoustic microscopy (PAM), optical-resolution photoacoustic microscopy (OR-PAM), and array-based PA imaging (array-PAI). In photoacoustic tomography (PAT) signals are collected from multiple transducer locations and reconstructed to form a tomographic image in a way similar to X-ray CT. In PAM, typically, a single element focused high-frequency ultrasound transducer is used to collect photoacoustic signals. A photoacoustic signal as a function of time (depth) is recorded for each position in a mechanically scanned trajectory to form a 3-D photoacoustic image. The maximum amplitude as a function of depth can be determined at each x-y scan position to form a maximum amplitude projection (MAP) C-scan image. Photoacoustic microscopy has shown significant potential for imaging vascular structures from macro-vessels all the way down to micro-vessels. It has also shown great promise for functional and molecular imaging, including imaging of nanoparticle contrast agents and imaging of gene expression. Multi-wavelength photoacoustic imaging has been used for imaging of blood oxygen saturation, by using known oxy- and deoxy-hemoglobin molar extinction spectra.

In traditional photoacoustic imaging, spatial resolution is due to ultrasonic focusing and can provide a depth-to-resolution ratio greater than 100. In OR-PAM, penetration depth is limited to ~1 mm in tissue (due to fundamental limitations of light transport) but resolution is micron-scale due to optical focusing. OR-PAM can provide micron-scale images of optical absorption in reflection-mode, in vivo, something that no other technique can provide. OR-PAM is capable of imaging blood vessels down to capillary size noninvasively. Capillaries are the smallest vessels in the body and so much crucial biology occurs at this level, including oxygen and nutrient transport. Much can go wrong at the capillary level too. In cancers, cells have an insatiable appetite for oxygen and nutrients to support their uncontrolled growth. They invoke a range of signaling pathways to spawn new vessels in a process known as angiogenesis and these vessels typically form abnormally. Tumors are often highly heterogeneous and have regions of hypoxia. Photoacoustic imaging has demonstrated the ability to image blood oxygen saturation (SO2) and tumor hypoxia in vivo.

In most photoacoustic and ultrasound imaging systems, piezoelectric transducers have been employed, in which an ultrasound coupling medium such as water or ultrasound gel is required. However for many clinical applications such as wound healing, burn diagnostics, surgery, and many endoscopic procedures physical contact, coupling, or immersion is undesirable or impractical.

The detection of ultrasound in photoacoustic imaging has, until recently, relied on ultrasonic transducers in contact with the biological tissue or an ultrasonic coupling agent both of which have major drawbacks as described above. Some detection strategies to solving the non-contact optical interferometric sensing problems associated with photoacoustic imaging have been reported.

Optical means of detecting ultrasound and photoacoustic signals have been investigated over a number of years; however, to date no technique has demonstrated practical non-contact in vivo microscopy in reflection mode with confocal resolution and optical absorption as the contrast mechanism.

One example of a low-coherence interferometry method for sensing photoacoustic signals was proposed in U.S. pregrant publication no. 2014/0185055 to be combined with an optical coherence tomography (OCT) system, resulting in 30 μm lateral resolution.

Another prior art system is described in U.S. pregrant publication no. 2012/0200845 entitled "Biological Tissue Inspection Method and System", which describes a noncontact photoacoustic imaging system for in vivo or ex vivo, non-contact imaging of biological tissue without the need for a coupling agent.

Other systems use a fiber based interferometer with optical amplification to detect photoacoustic signals and form photoacoustic images of phantoms with acoustic (not optical) resolution. However these systems suffer from a poor signal-to-noise ratio, other contact-based photoacoustic systems offer significantly improved detection capabilities, in vivo imaging was not demonstrated, and optical-resolution excitation was not demonstrated.

Industrial laser ultrasonics has used interferometry to detect acoustic signatures due to optical excitation of inanimate objects for non-destructive testing. This approach has been adapted to detect ultrasound ex vivo in chicken breast and calf brain specimens, however, optical-resolution focusing of the excitation light was not examined.

Laser Doppler vibrometry has been a powerful non-contact vibration sensing methodology, however, weak signal-to-noise and poor image quality have proven to be a limitation when sensing deep-tissue signals from broadbeam photoacoustic excitation.

Similarly, Mach Zehnder interferometry and two-wave mixing interferometry have been used previously for sensing photoacoustic signals. However many such techniques still require direct contact or fluid coupling; have not offered in vivo studies or optical resolution for phantom studies.

BRIEF SUMMARY

According to an aspect, there is provided a photoacoustic remote sensing system (PARS) for imaging a subsurface structure in a sample, where the PARS comprises an excitation beam configured to generate ultrasonic signals in the sample at an excitation location; an interrogation beam incident on the sample at the excitation location, a portion of the interrogation beam returning from the sample that is indicative of the generated ultrasonic signals; an optical system that focuses the excitation beam at a first focal point and the interrogation beam at a second focal point, the first and second focal points being below the surface of the sample; and an interferometer that detects the returning portion of the interrogation beam.

According to another aspect, there is provided a photoacoustic remote sensing system (PARS) for imaging a subsurface structure in a sample, where the PARS comprises an excitation beam configured to generate ultrasonic signals in the sample at an excitation location; an optical system that focuses the excitation beam with a focal point that is below the surface of the sample; an interrogation beam directed toward an optical element that is responsive to the ultrasonic signals, the optical element being interposed between the sample and the interrogation beam, wherein the generated ultrasonic signals are characterized by a returning portion of the interrogation beam; and an interferometer that detects the returning portion of the interrogation beam. The optical element may be a Fabry Perot element. The interferometer may detect ultrasonic signals to a depth of 7 cm within the sample According to another aspect, there is provided an endoscopic device that uses a photoacoustic remote sensing system (PARS) for imaging a subsurface structure in a sample, the endoscopic device comprising a fiber optic cable having an input end and a detection end; an excitation beam coupled to the input end of the fibre optic cable, wherein in use the excitation beam generates ultrasonic signals in the sample at an excitation location that is adjacent to the detection end of the fiber optic cable, the fiber optic cable focusing the excitation beam at a first focal point that is below the surface of the sample; an interrogation beam coupled to the input end of the fibre optic cable and incident on the excitation location, the fiber optic cable focusing the excitation beam at a first focal point that is below the surface of the sample, and wherein a portion of the interrogation beam that is indicative of the generated ultrasonic signals is received by the detection end of the fiber optic cable and travels to the input end; and an interferometer that receives the returning portion of the interrogation beam at the input end of the fiber optic cable.

According to other aspects, either alone or in combination, as applicable: the first and second focal points may be within 1 mm of the surface of the sample; the first and second focal points may be greater than 1 µm below the surface of the sample; the focal point may be spaced below the surface of the sample at a depth that is greater than a focal zone of the respective at least one of the excitation beam and the interrogation beam; the excitation beam and the interrogation beam have a lateral separation of less than 1 mm or less than 0.5 mm on the sample; the excitation beam may have a focal point that is laterally within the focal zone of the interrogation beam; the interrogation beam may have a focal point that is laterally within the focal zone of the excitation beam; there may be a processor that calculates an image of the sample based on the returning portion of the interrogation beam; at least one of the first focal point and the second focal point may have a focal diameter of less than 30 µm, 10 µm, or 1 µm; the excitation beam may be scanned through the sample while the interrogation beam is stationary; the interrogation beam may be scanned through the sample while the excitation beam is stationary; and each of the interrogation beam and the excitation beam may be scanned through the sample concurrently.

Other aspects will be apparent from the description and claims below.

BRIEF DESCRIPTION OF THE SEVERAL VIEW OF THE DRAWINGS

These and other features will become more apparent from the following description in which reference is made to the appended drawings, the drawings are for the purpose of illustration only and are not intended to be in any way limiting, wherein.

Figure 10A:
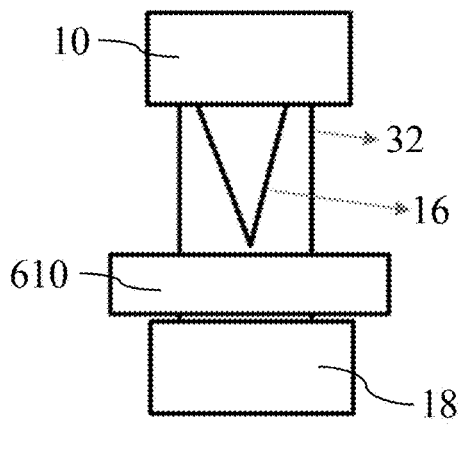
Figure 10B:
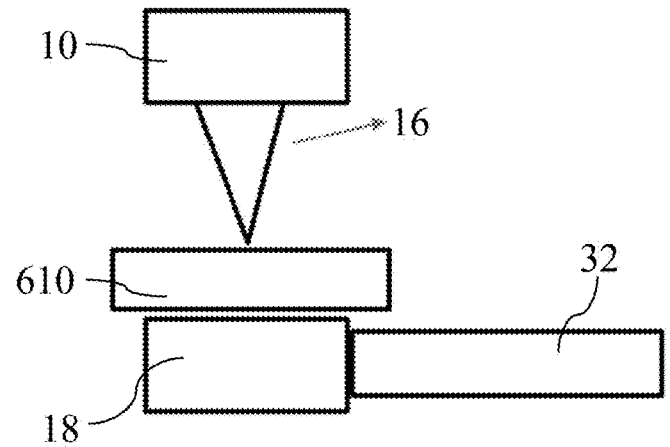
Figure 10C:
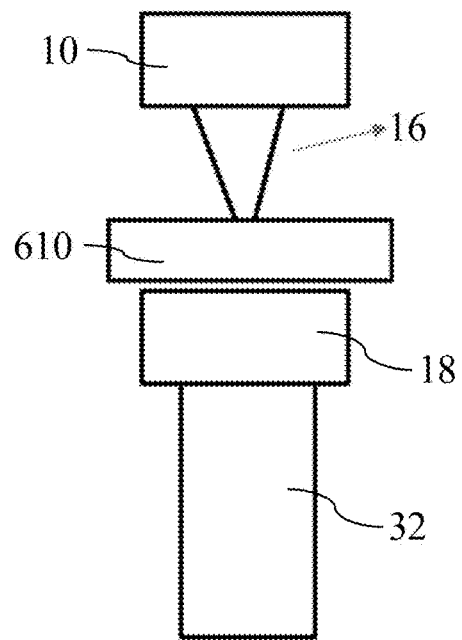

FIGS. 10A, 10B, and 10C are block diagrams of examples of sensing system using a Fabry-Perot interferometer.

Figure 11A:
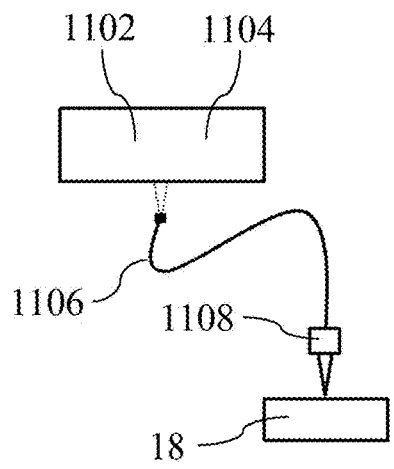
Figure 11B:
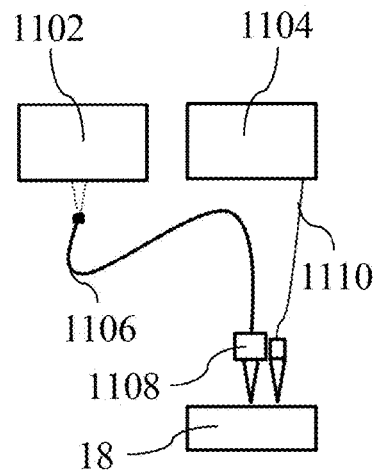
Figure 11C:
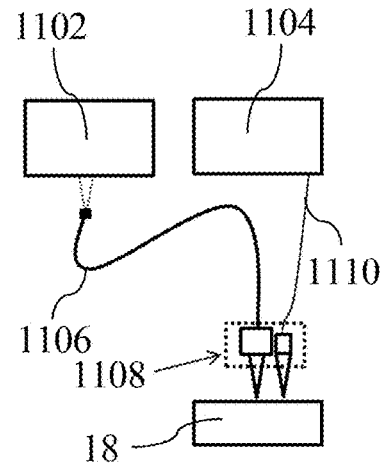

FIGS. 11A, 11B, and 11C are block diagrams of examples of sensing systems in an endoscopy configuration.

Figure 12:
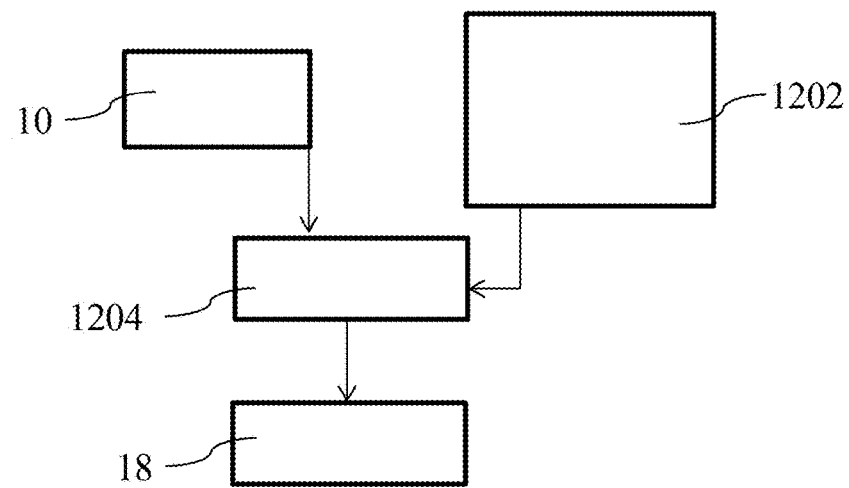

FIG. 12 is a block diagram of a sensing system integrated with another optical imaging system.

Figure 13A:
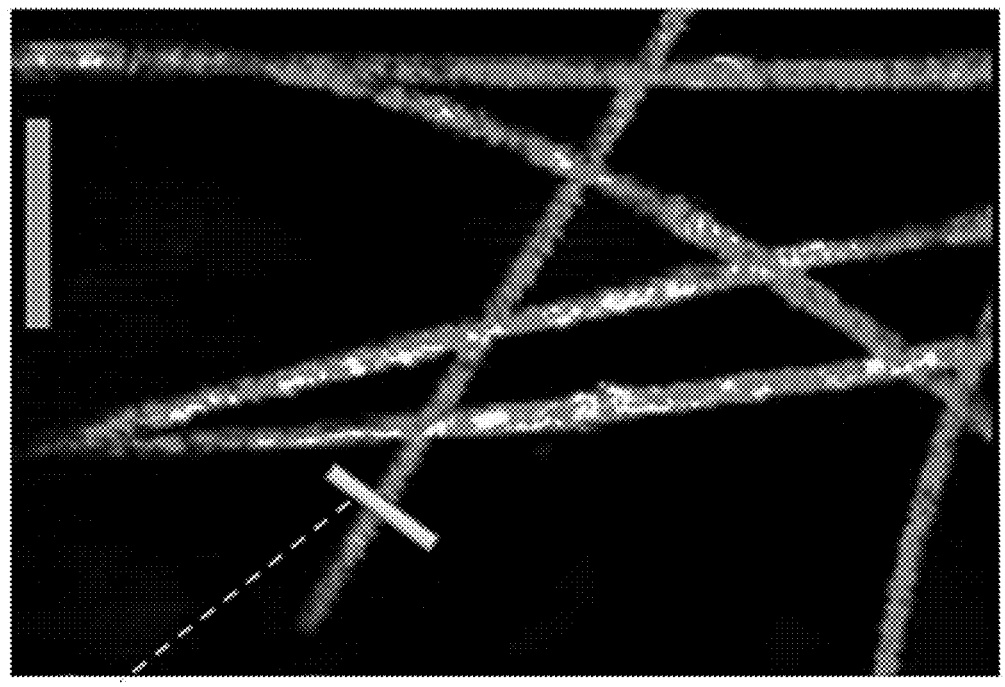

FIG. 13A is a PARS image of a network of carbon fibres.

Figure 13D:
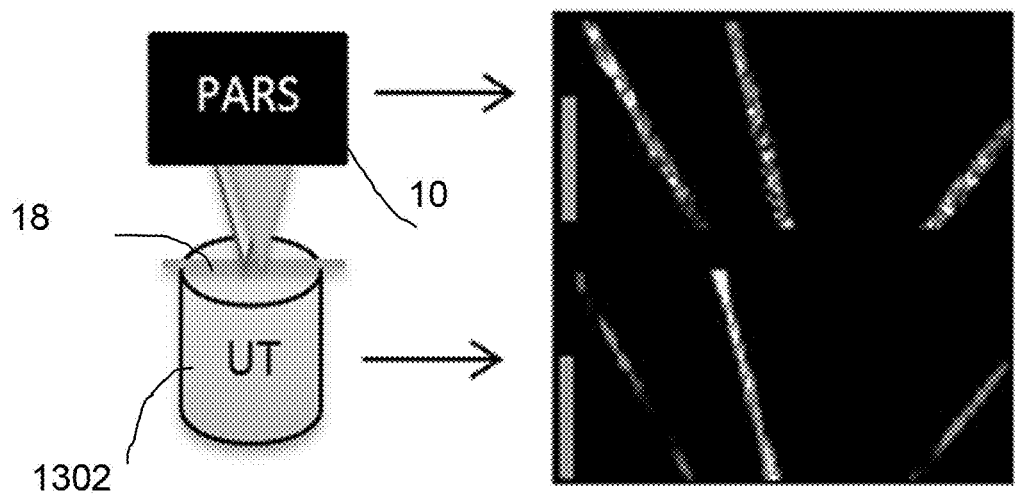
Figure 13B:
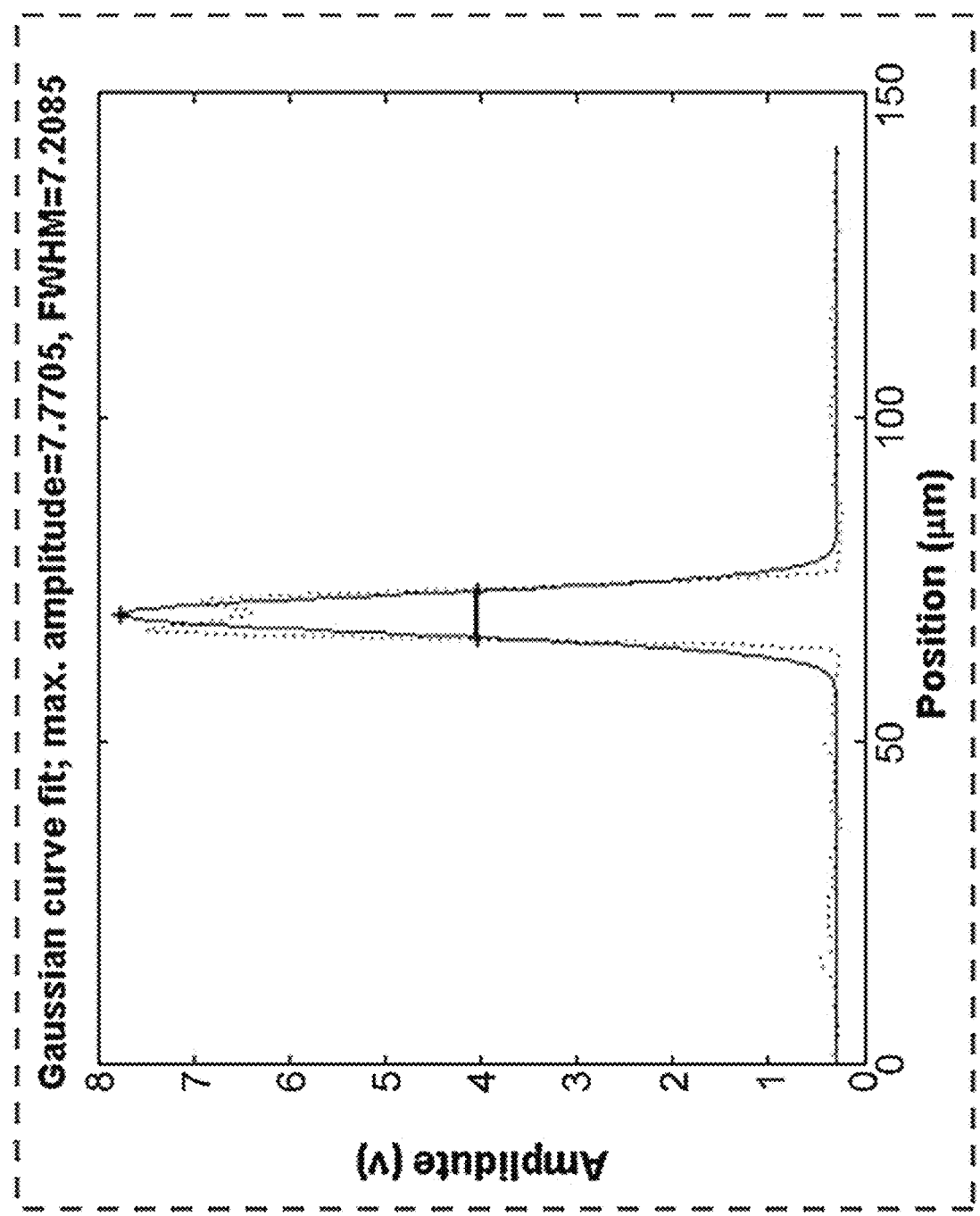

FIG. 13B is a graph of the FWHM obtained by fitting an individual carbon fiber signal amplitude to a Gaussian function.

Figure 13C:
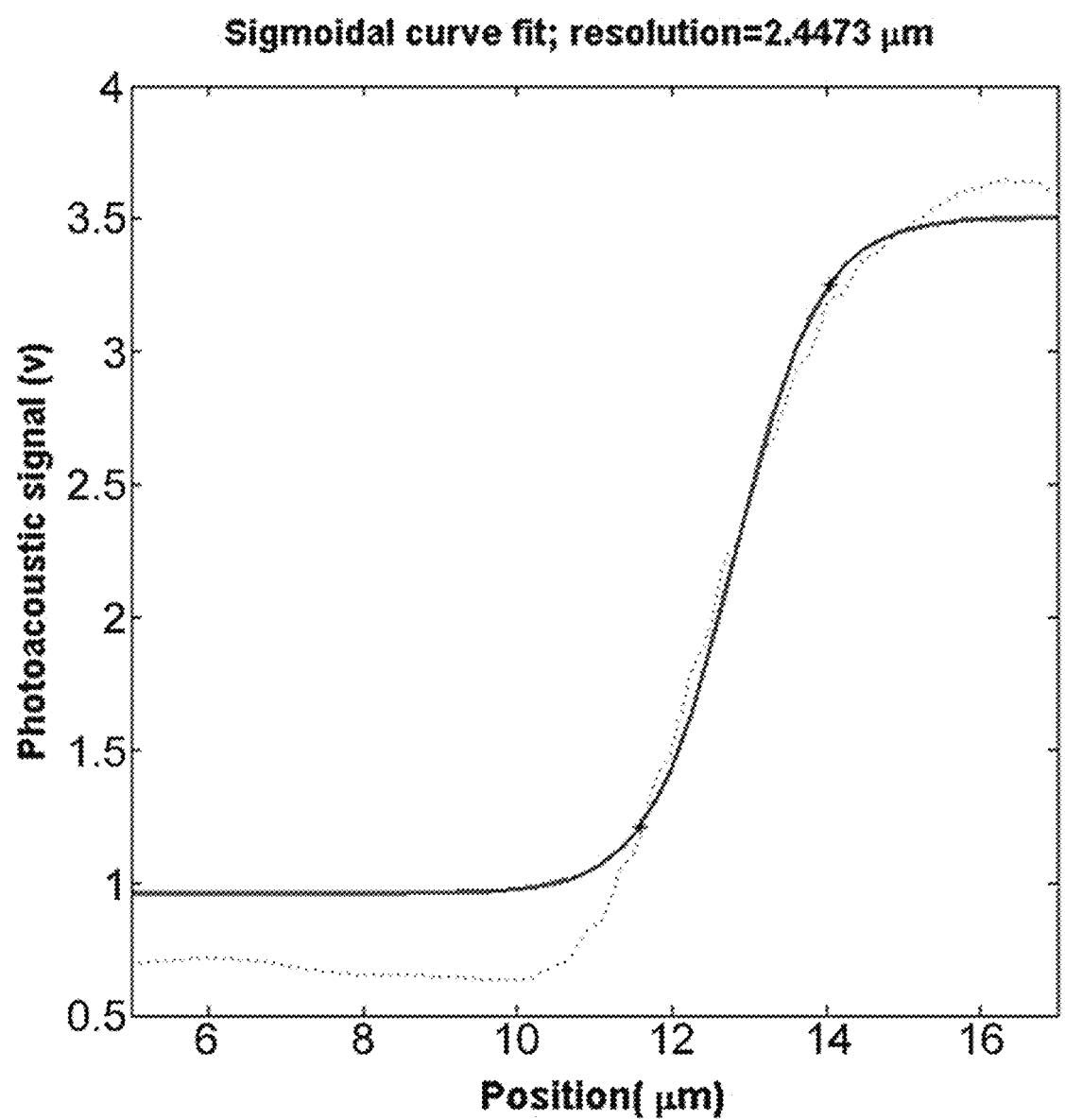

FIG. 13C is a graph of the resolution using a knife edge spread function.

FIG. 13D is a comparison of images obtained by sensing systems in reflection mode and transmission mode.

FIGS. 14A, 14B, 1C, and 14D are in vivo images of CAM-membrane of 5-day chicken embryos.

Figure 15:
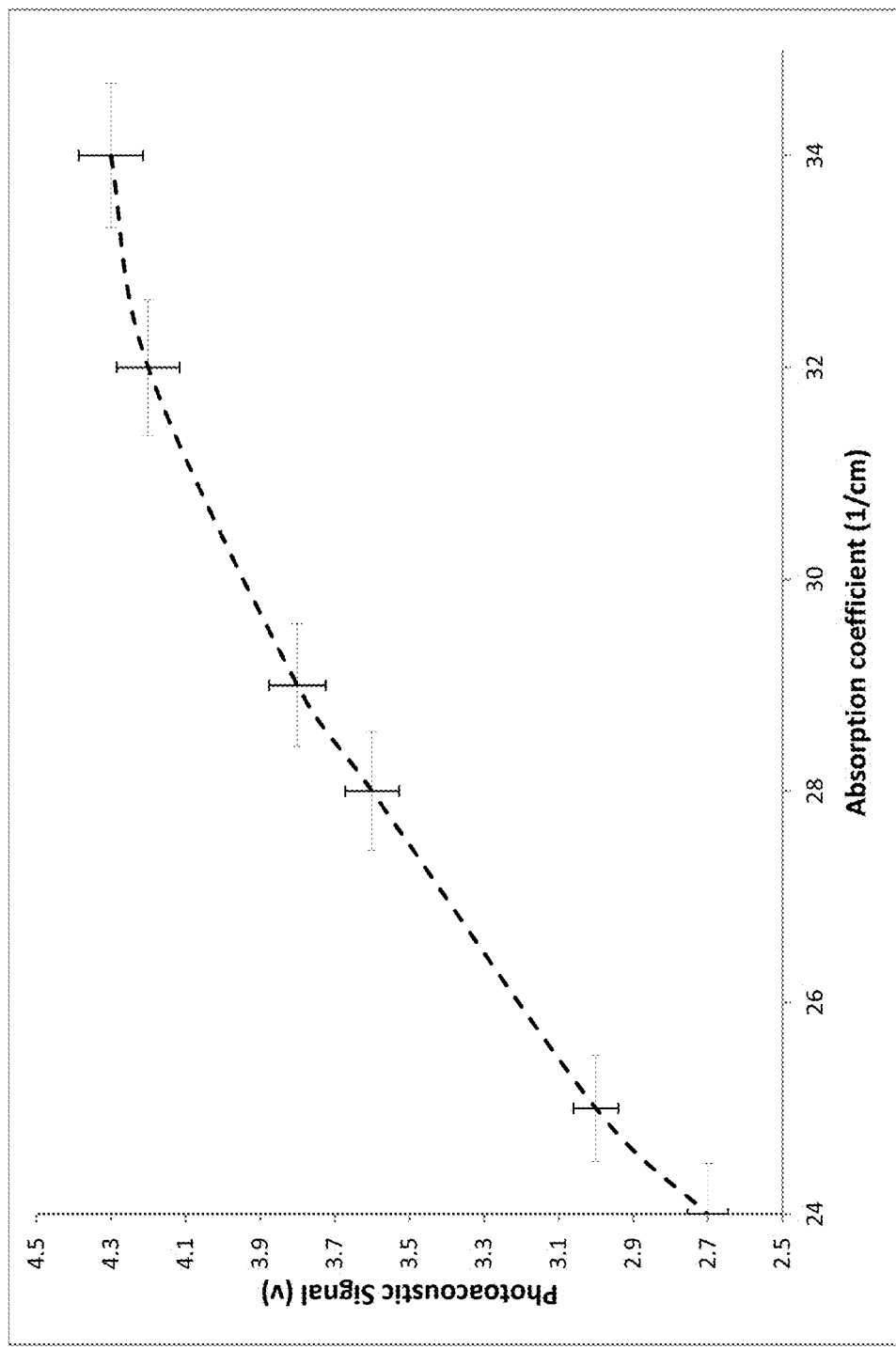

FIG. 15 is a chart of the measured photoacoustic signals from various dye concentrations.

Figure 16:
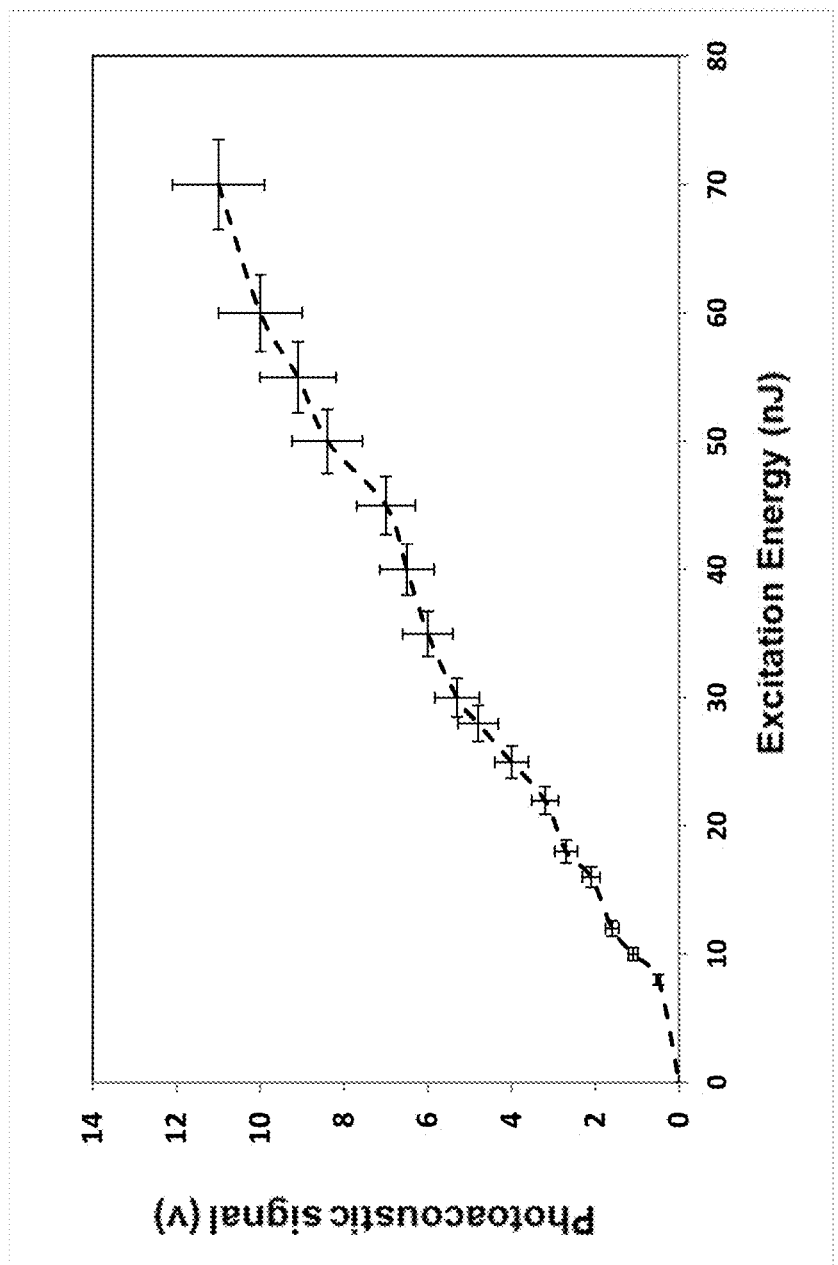

FIG. 16 is a graph of the photoacoustic signal vs. excitation energy on the sample when interrogation power is fixed at 8 mW.

Figure 17:
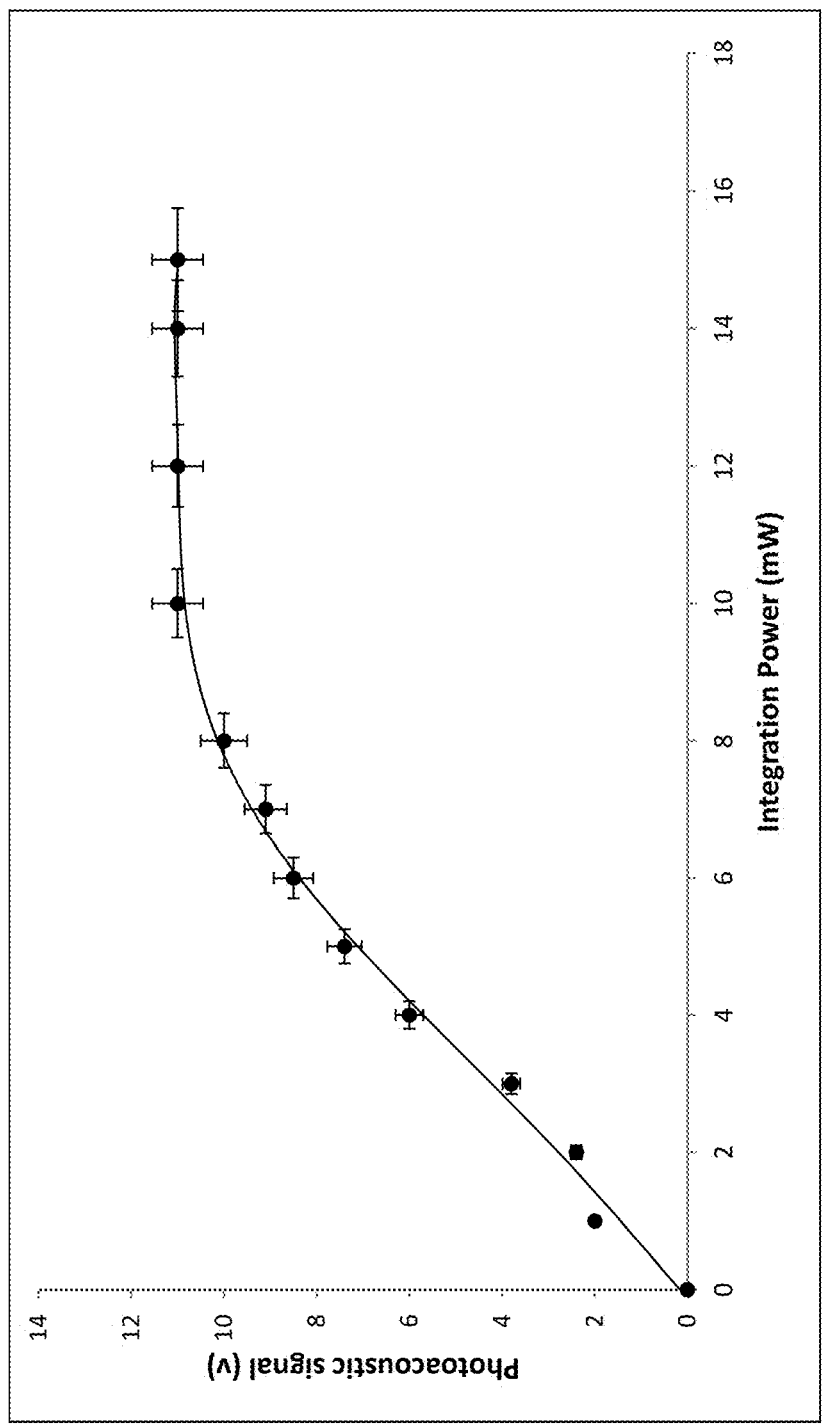

FIG. 17 is a graph of the photoacoustic signal vs. interrogation power on the sample when excitation energy is fixed at 60 nJ.

Figure 18A:
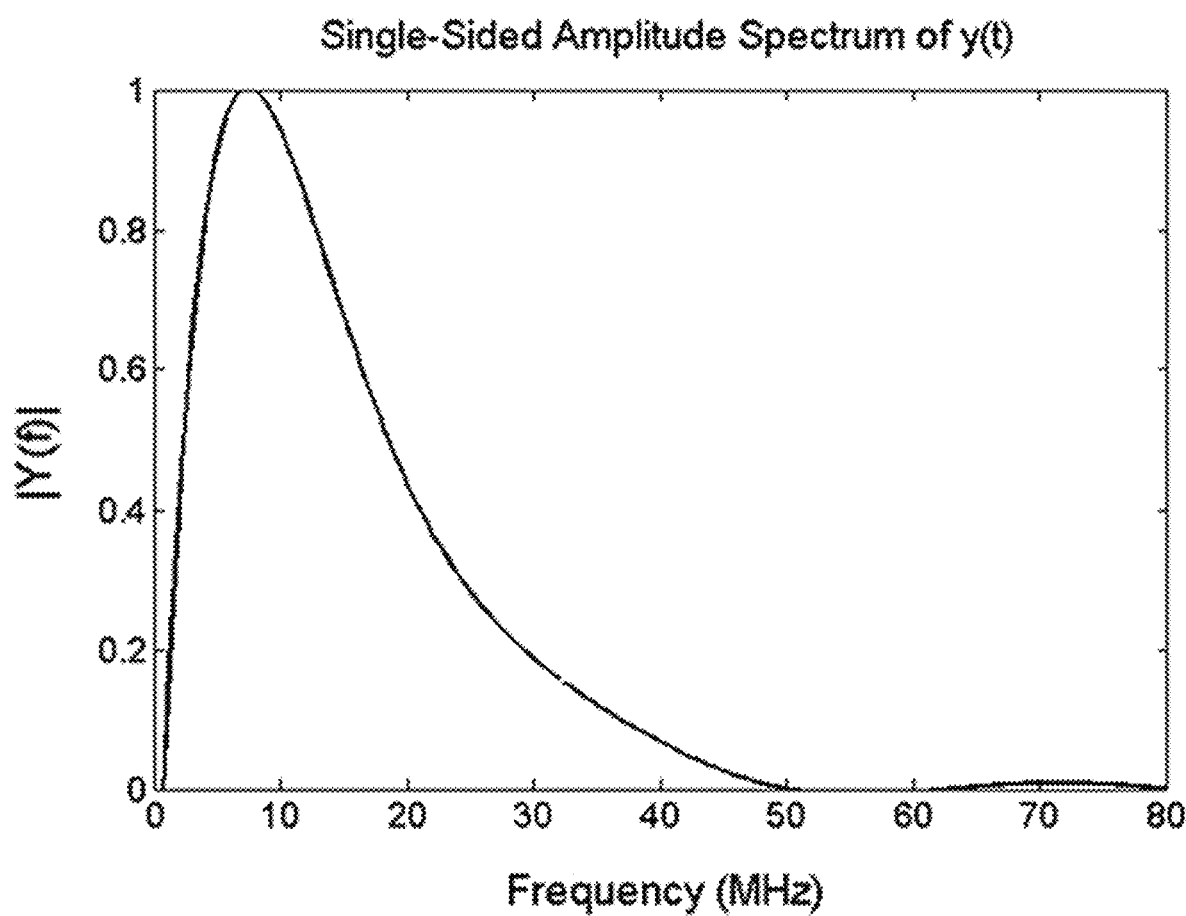

FIG. 18A depicts an example of the frequency response of a PARS system.

Figure 18B:
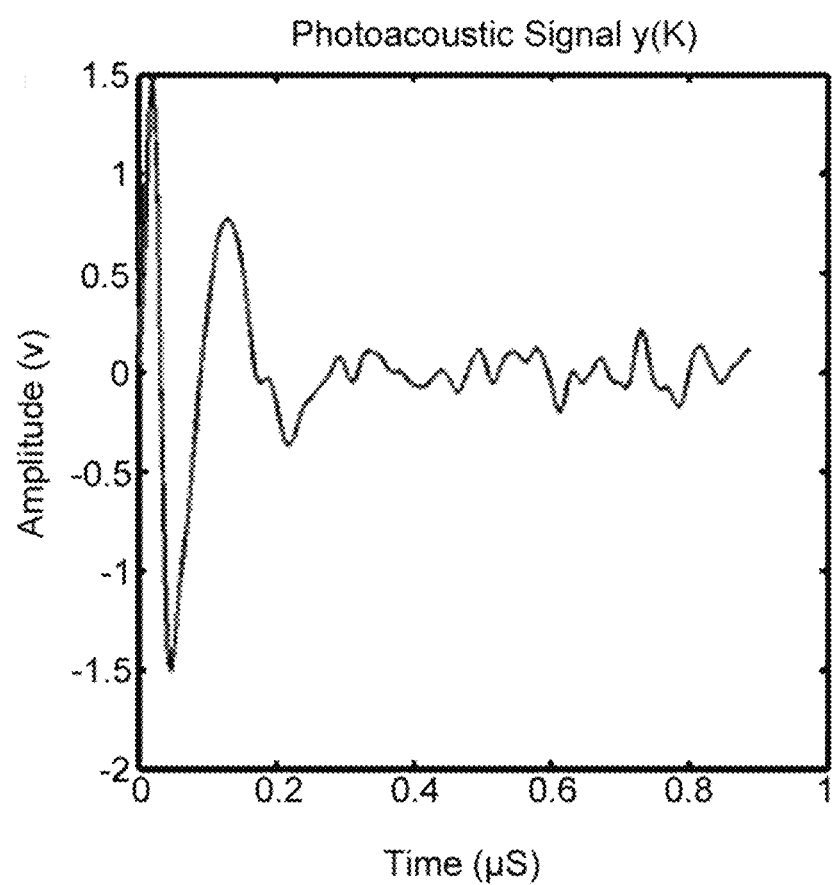

FIG. 18B depicts an example of the photoacoustic time domain signal of an individual carbon fiber using a PARS system.

Figure 18C:
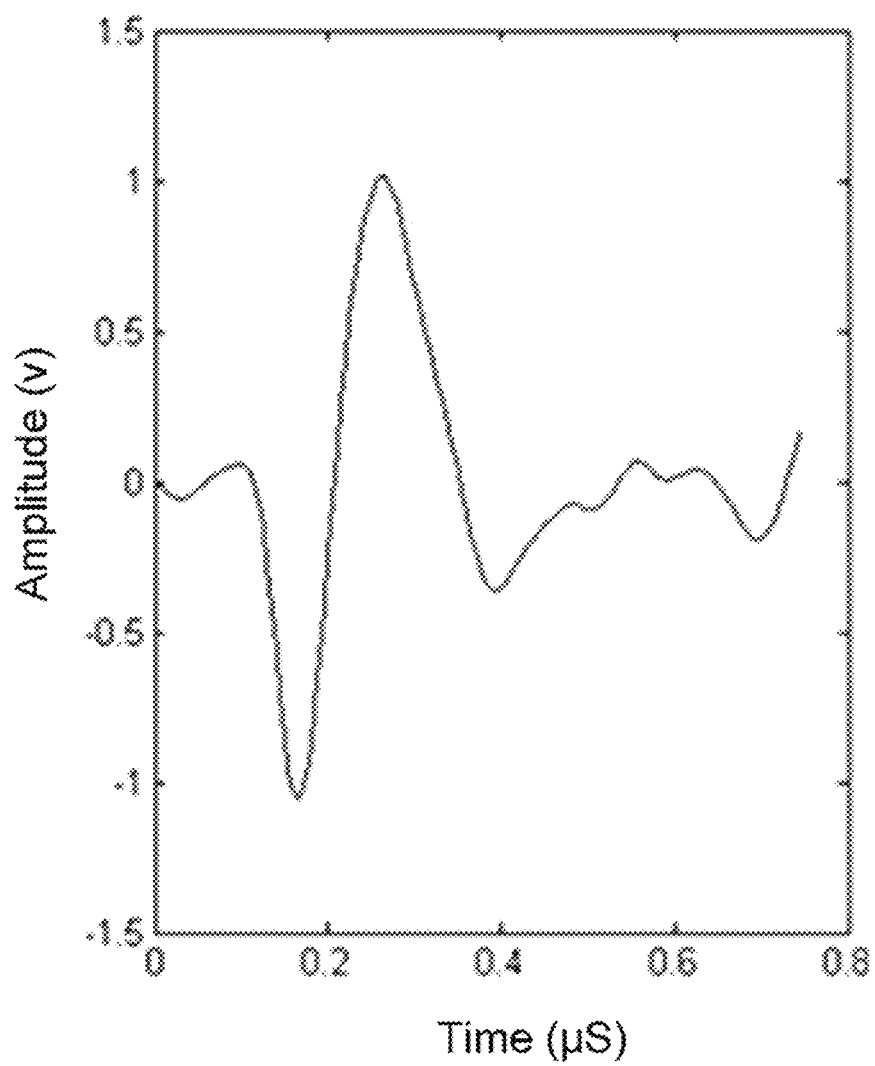
Figure 18D:
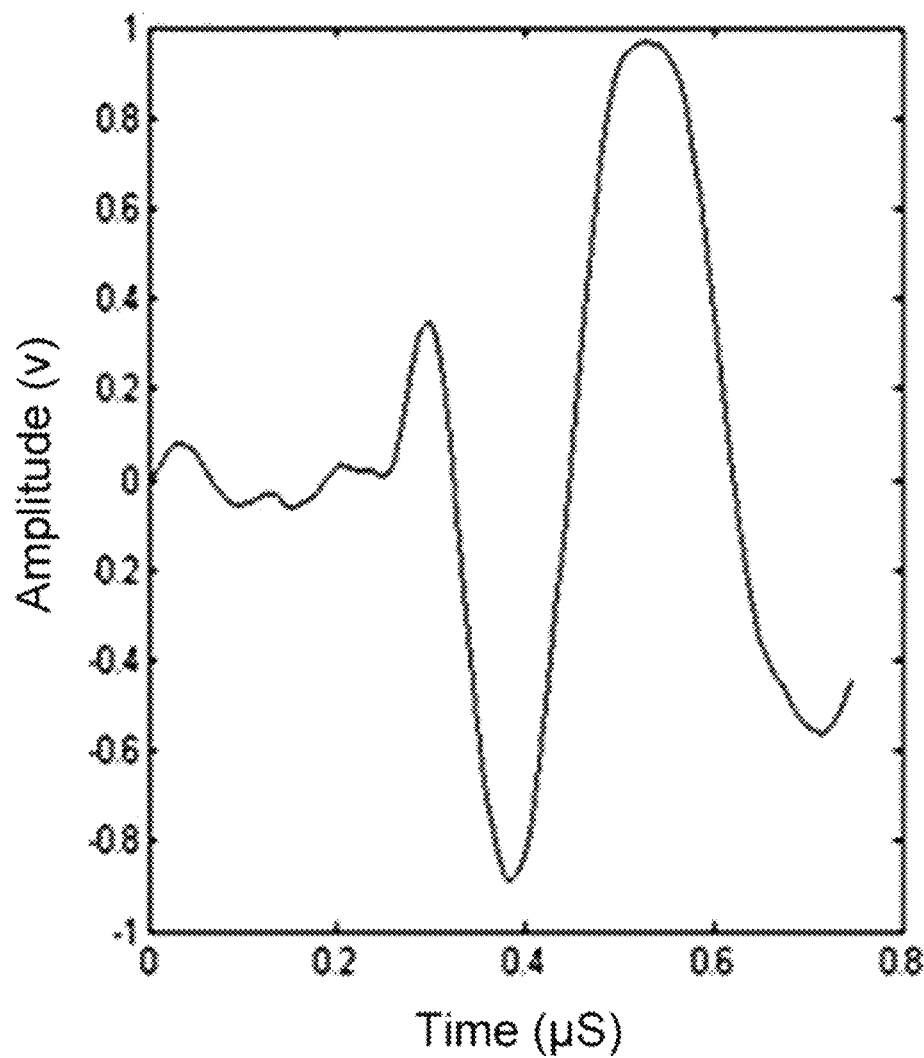
Figure 19B:
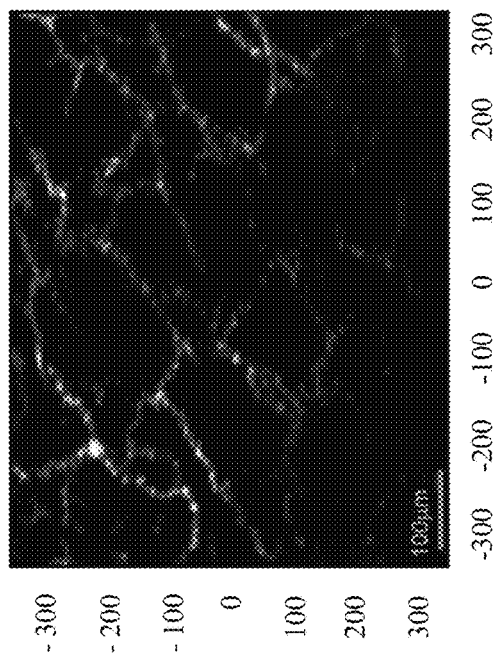
Figure 19D:
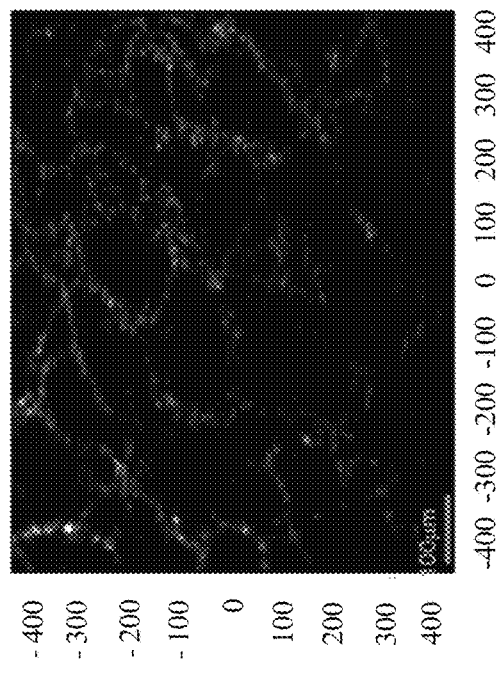
Figure 19A:
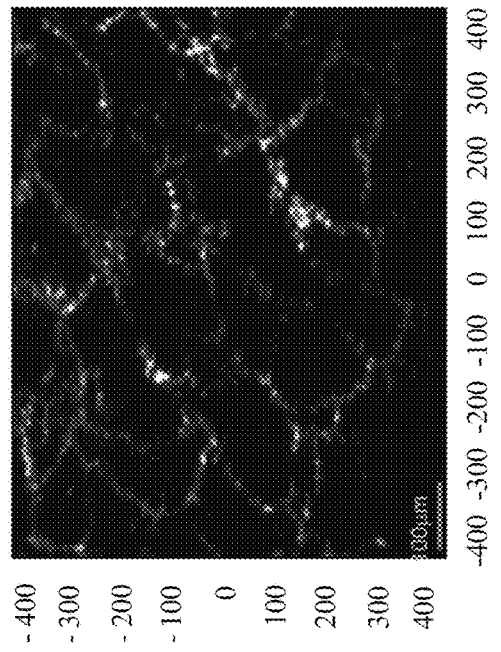
Figure 19C:
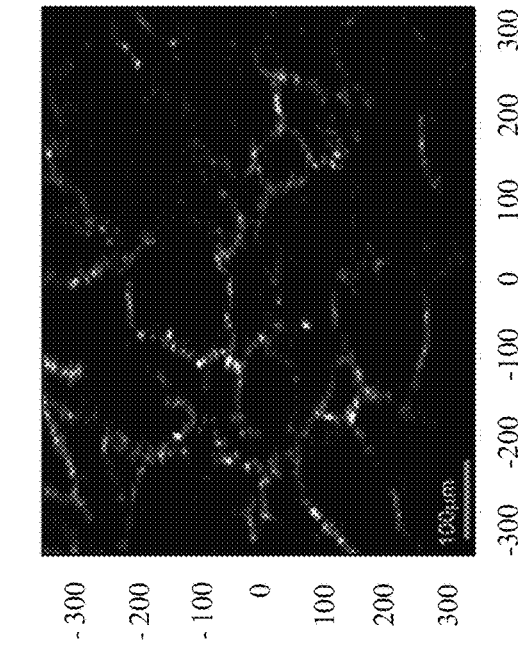

FIGS. 18C and 18D depict an example of the photoacoustic time domain signal of an individual carbon fiber using a PARS system when the excitation and interrogation beams are separated by ~120 and 330 µm, respectively.

FIGS. 19A, 19B, 19C, and 19D depict in vivo PARS images of a mouse ear.

Figure 20:
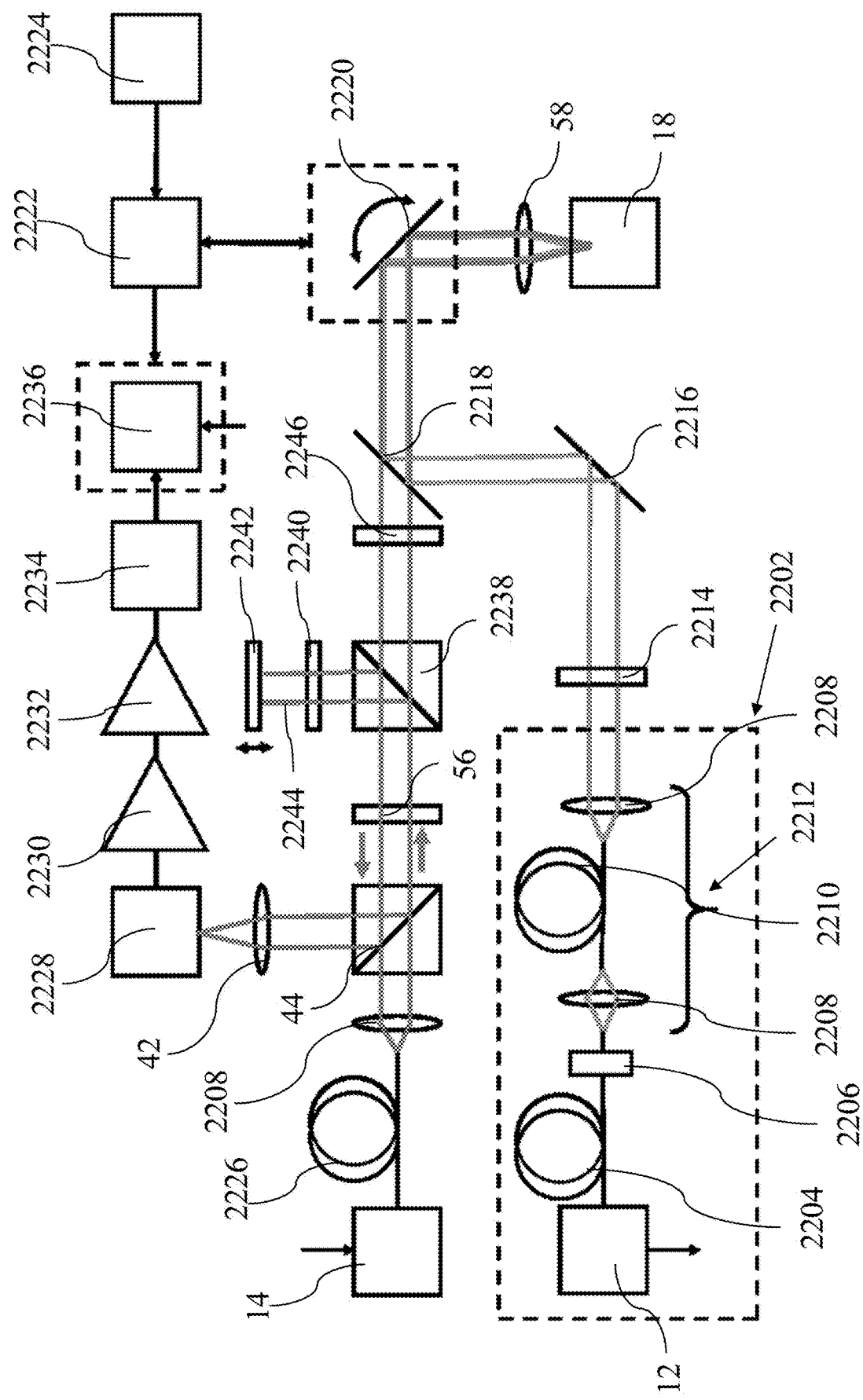
Figure 21:
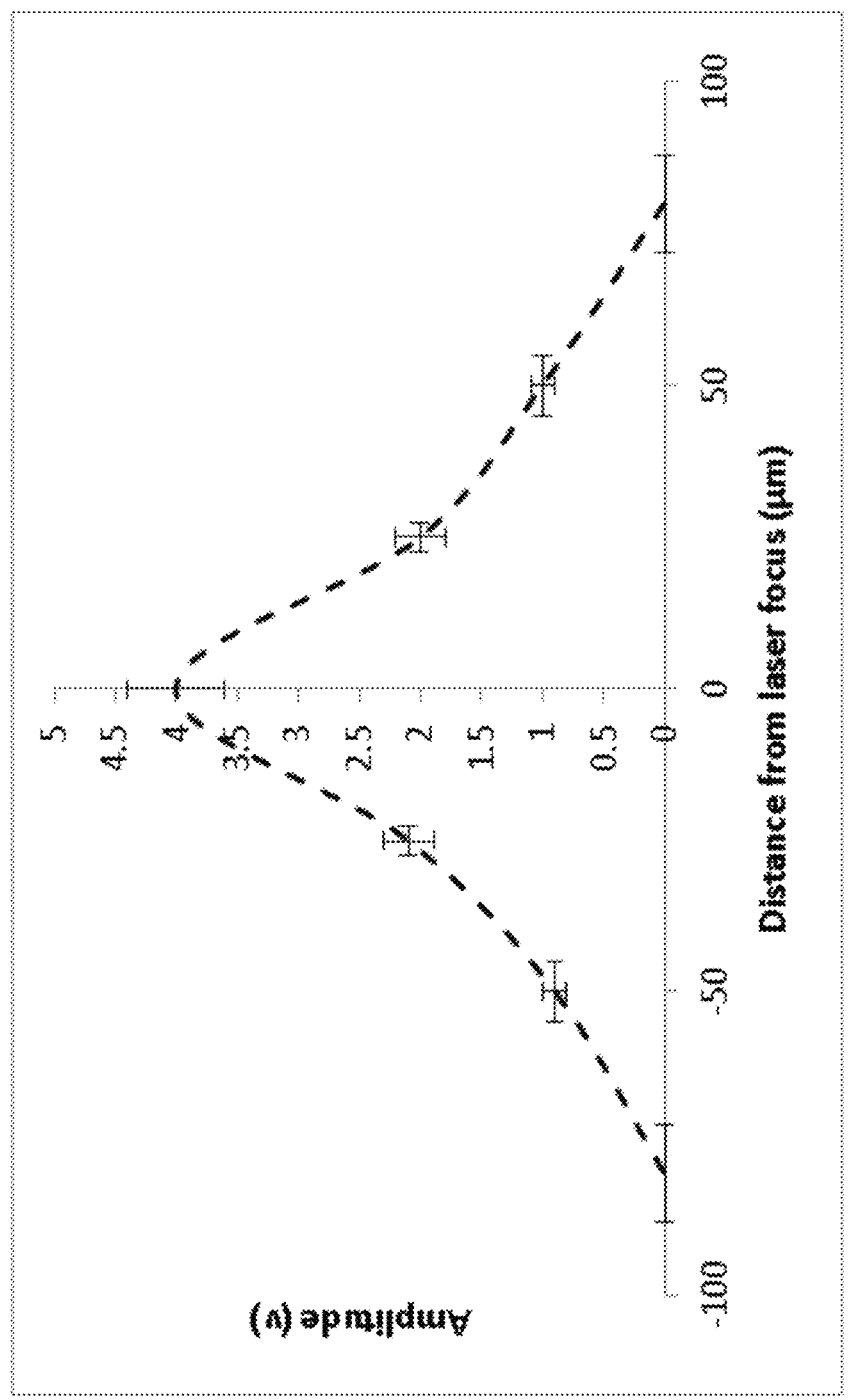

FIG. 20 is a block diagram of a system using a modified version of polarization sensitive Michelson interferometry FIG. 21 is a graph of the measure signal from an unfocused transducer at different lateral distances.

Figure 22:
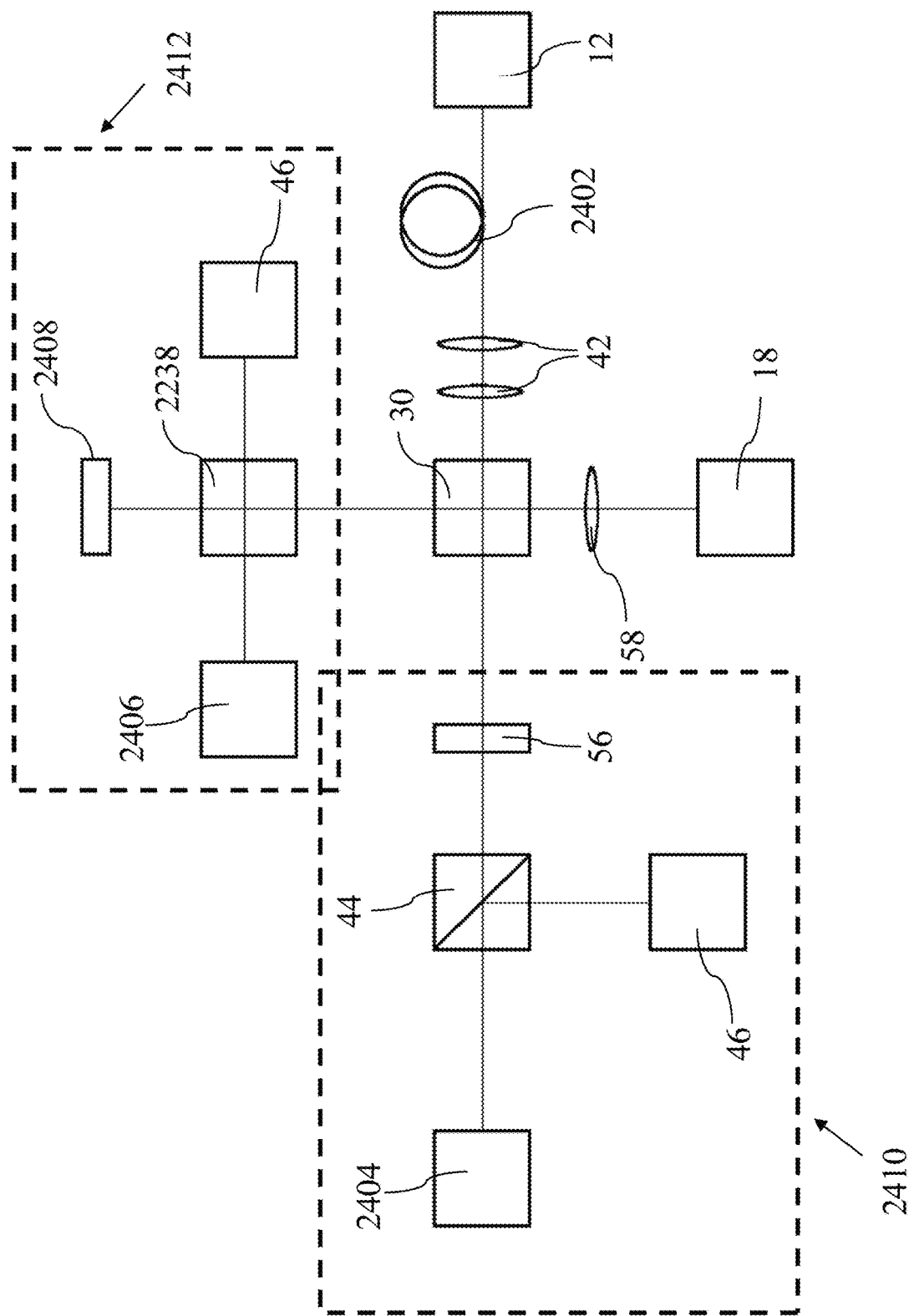

FIG. 22 is a block diagram of a scanning system with two different interferometry designs for use with the interrogation beam.

FIGS. 23A, 23B, 23C, and 24 are images of a rat's ear.

DETAILED DESCRIPTION

Photoacoustic imaging is an emerging biomedical imaging modality that uses laser light to excite tissues. Energy absorbed by chromophores or any other absorber is converted to acoustic waves due to thermo-elastic expansion. These acoustic signals are detected and reconstructed to form images with optical absorption contrast. Photoacoustic imaging (PA) has been shown to provide exquisite images of microvessels and is capable of imaging blood oxygen saturation, gene expression, and contrast agents, among other uses. In most PA and ultrasound imaging systems piezoelectric transducers have been employed, in which an ultrasound coupling medium such as water or ultrasound gel is required. However for many clinical applications such as wound healing, burn diagnostics, surgery, and many endoscopic procedures physical contact, coupling, or immersion is undesirable or impractical. The system described herein is capable of in vivo optical-resolution photoacoustic microscopy using non-contact optical interferometric sensing without use of any ultrasound medium.

The system described herein, a photoacoustic remote sensing (PARS) microscopy system, is based on the idea of focusing excitation light to a near diffraction-limited spot and detecting photoacoustic signals using a confocal interrogation beam co-focused with the excitation spot. While previous approaches used a broad excitation beam with powerful lasers delivering mJ-J of pulse energy over a broad area, the PARS microscopy technique described herein uses nJ-scale pulse energies focused to near diffraction-limited spots. When focusing into tissue, the surface fluence can be maintained below present ANSI limits for laser exposure but the ballistically-focused light beneath the tissue can create fluences transiently far above the ANSI limits (as is done in other microscopy methods). In PARS, this means that very large local fluences ~J/cm$^2$ are created within a micron-scale spot, generating very large initial acoustic pressures. For example, at 532-nm excitation wavelength, imaging a capillary with 500 mJ/cm$^2$ local fluence would result in an initial pressure on the order of 100 MPa locally. However, because this large pressure is initially localized to a micron-scale spot, by the time the signals are detected by a fluid-coupled detector ~1 cm away, the signals are reduced by 1/r diffractive losses and attenuation to ~KPa scales. Signals can be orders of magnitude less for acoustic-resolution photoacoustic imaging where unfocused excitation beams are used, ANSI limits for visible light is 20 mJ/cm$^2$, and greater imaging depths are explored. Large numerical aperture focused acoustic detection is required for optimal signal-to-noise in OR-PAM to ensure the maximal energy collection. In PARS approach, large optically-focused photoacoustic signals are detected as close to the photoacoustic source as possible, which is done optically by co-focusing an interrogation beam with the excitation spot. A long-coherence length interrogation laser is preferably used with low amplitude and phase noise to read-out the large local photoacoustic vibrations interferrometrically using a novel architecture designed to optimize received signal intensities.

The high sensitivity and the fine resolution of the proposed system offer performance comparable to other in vivo optical resolution photoacoustic microscopy systems but in a non-contact reflection mode suitable for many clinical and pre-clinical applications.

Figure 1:
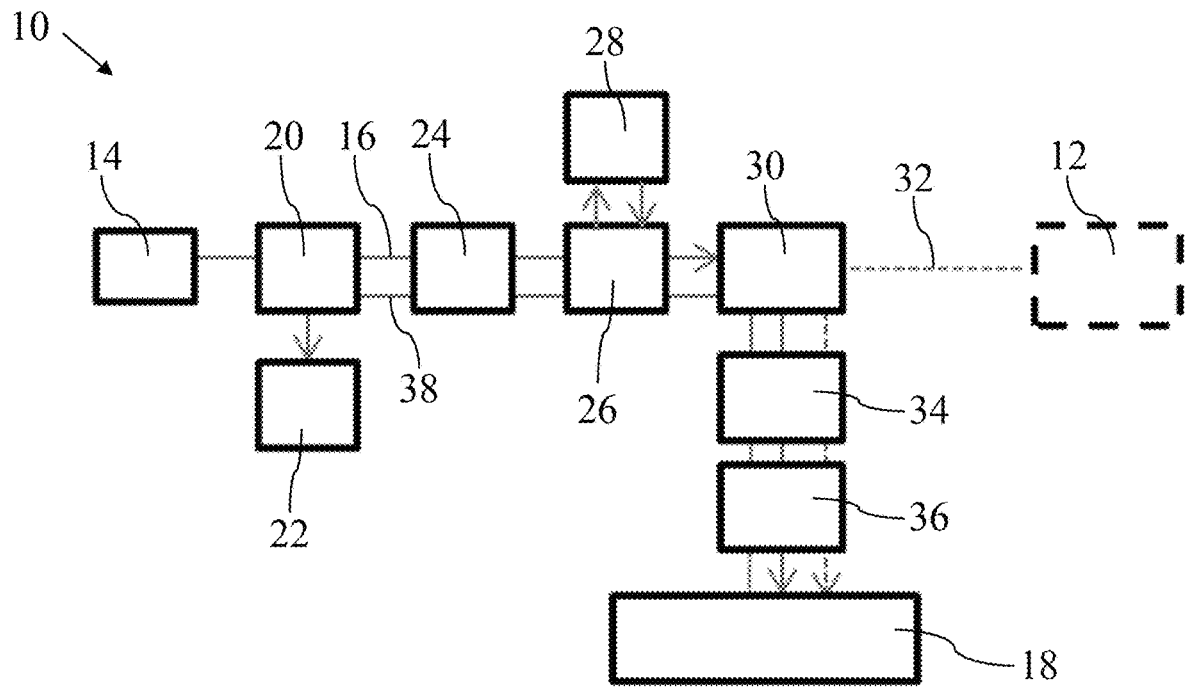
FIG. 1 through 4 are block diagrams of optical-resolution photoacoustic remote sensing (OR-PARS) microscopy systems

Some of the possible options of the optical-resolution photoacoustic remote sensing (OR-PARS) microscopy system are depicted in FIG. 1 through 4. Variations to the depicted systems will be apparent to those skilled in the art. Referring to FIG. 1, a block diagram of PARS system 10, and in particular, an optical-resolution photoacoustic remote sensing (OR PARS) microscopy system, is shown. A multi-wavelength fiber excitation laser 12 is used in multi focus form to generate photoacoustic signals. Excitation laser 12 preferably operates in the visible spectrum, although the particular wavelength may be selected according to the requirements of the particular application. The acoustic signatures are interrogated using a long-coherence length probe beam 16 from a detection laser 14 that is co-focused and co-aligned with the excitation spots on sample 18. The probe beam 16 passes through a beam splitter 20 that transfers a portion of the signal to a detection unit 22. Probe beam 16 passes through a polarization control/beam quality unit 24 and a second beam splitter 26 that ties in a reference beam provider 28. Probe beam 16 then passes through a beam combiner unit 30 that also directs excitation beam 32 through a scanning device 34 and a focusing device 36 before reaching sample 18. The reflected beam 38 returns along the same path and is analyzed by detection unit 22.

A modified version of polarization sensitive Michelson interferometry has been employed to remotely record the large local initial pressures from chromophores and without appreciable acoustic loses. The PARS microscopy system offers optical lateral resolution down to sub-µm.

Figure 2:
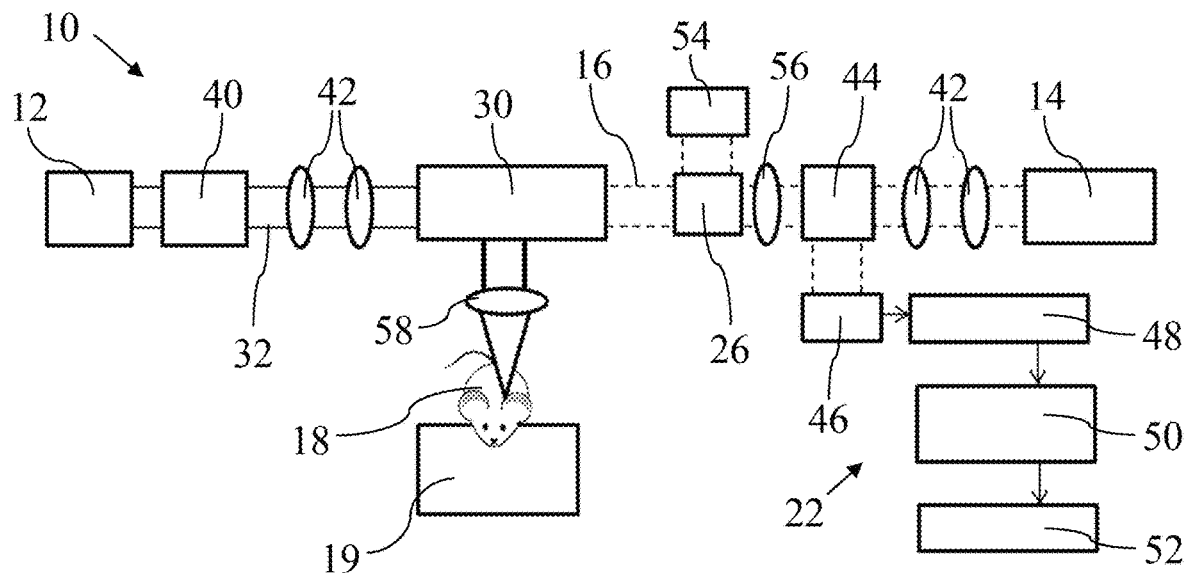
Figure 3:
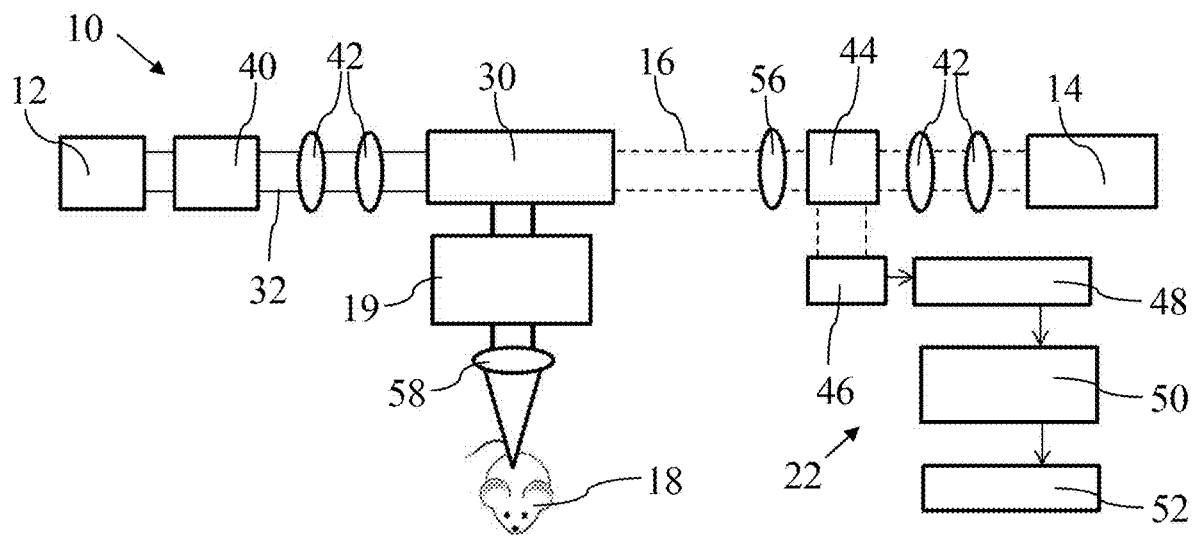
Figure 4:
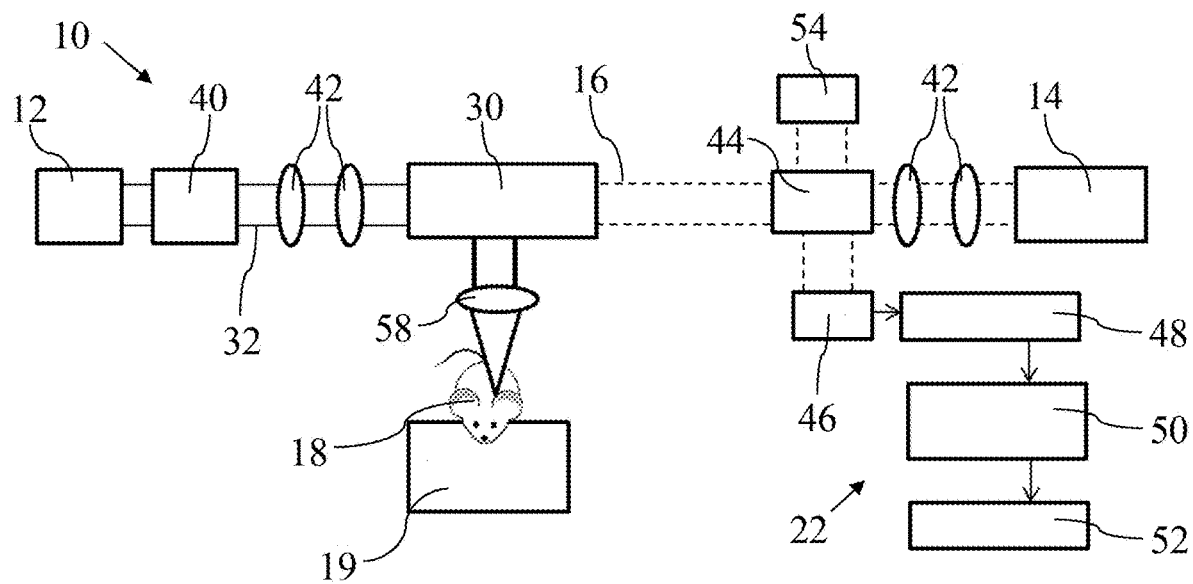

Referring to FIG. 2, an example of a PARS experimental setup is shown, with a multi wavelength unit 40 placed in series with the excitation laser 12 and a lens system 42. Detection laser 14 is placed in series with a lens system 42 and a beam splitter 26 that is preferably a polarized beam splitter. As depicted, detection unit 22 is made up of a photodiode 46, amplifier 48, data acquisition unit 50 and a computer 52. A portion of beam 16 is redirected by beam splitter 26 to a neutral density filter 54 after passing through a quarter wave plate 56. Excitation beam 32 and probe beam 16 are combined by beam combiner unit 30 and directed to sample 18 by an objective lens 58. Sample 18 may be placed on a scanning unit 19, allowing for sample 18 to be moved and to allow scanning. FIG. 3 depicts another example of a PARS experimental setup using common path interferometry, but without second beam splitter 26 or neutral density filter 54. FIG. 3 shows scanning unit 19 placed between beam combiner unit 30 and objective lens 58, allowing for the beam to be moved to allow scanning rather than moving sample 18. FIG. 4 depicts a further example of a PARS experimental setup using Michelson interferometry, where quarter wave plate 56 has been omitted, and beam splitter 44 is used to redirect a portion of beam 16 to both neutral density filter 54 and detection unit 22.

It will be apparent that other examples may be designed with different components to achieve similar results. For example, other examples could include all-fiber architectures where circulators replace beamsplitters similar to optical-coherence tomography architectures. Other alternatives may include longer coherence length sources, use of balanced photodetectors, interrogation-beam modulation, incorporation of optical amplifiers in the return signal path, etc.

The OR-PARS system takes advantage of two focused laser beams on the sample which can simulate a confocal OR-PAM configuration. Since there are optical components between the objective lens 58 and the sample 18, optical aberrations can be minimized.

Unlike OCT, PARS can take advantage of a high coherence interrogation beam (HC). In the low coherence interferometry (LC), backscattering light is detected from a selected depth (via coherence gating). However in HC method signal from all depth can be detected. Combination of HC detector with multi-focus excitation improves the SNR.

The OR-PARS takes advantage of optical excitation and detection which can help dramatically reduce the footprint of the system. The absence of a bulky ultrasound transducer makes this all optical system suitable for integrating with other optical imaging systems. Unlike previous non-contact photoacoustic imaging systems, the OR-PARS system is capable of in vivo imaging. It relies on much simpler setup and takes advantage of recording the large initial ultrasound pressures without appreciable acoustic loses.

During in vivo imaging experiments, no agent or ultrasound coupling medium are required. Unlike many other interferometric sensors PARS does not require a floating table. No special holder or immobilization is required to hold the target during imaging sessions.

PARS can be used to detect ultrasound signals directly. The PARS system is capable of detecting noncontact measurement of the displacement caused by ultrasound signals from an ultrasound transducer. In one example, a small amount of water was used at the top of the transducer and the transducer was driven by a sine wave from a function generator at 10 MHz, and produced a noise equivalent pressure of 1 KPa.

Other advantages that are inherent to the structure will be apparent to those skilled in the art. The embodiments described herein are illustrative and not intended to limit the scope of the claims, which are to be interpreted in light of the specification as a whole.

A pulse laser is used to generate photoacoustic signals and the acoustic signatures are interrogated using either a long-coherence or short-coherence length probe beam co-focused with the excitation spots. The PARS system is utilized to remotely record the large local initial pressures from chromophores and without appreciable acoustic loses due to diffraction, propagation and attenuation.

The excitation beam may be any pulsed or modulated source of electromagnetic radiation including lasers or other optical sources. In one example, a nanosecond-pulsed laser was used. The excitation beam may be set to any wavelength suitable for taking advantage of optical (or other electromagnetic) absorption of the sample. The source may be monochromatic or polychromatic.

The receiver beam, or interrogation beam, may be a long-coherence or a short-coherence length probe beam. In one example discussed above, the probe beam/receiver beam had a linewidth significantly less than the frequency of signals detected. Preferably, the interrogation beam has a coherence length selected so that the line width of the laser is less than the acoustic signal bandwidth or detection bandwidth PARS with a long-coherence beam may be integrated with OCT to provide a complete set of information offered by both photoacoustic and OCT systems.

PARS with a short or long-coherence beam may be used for either optical resolution photoacoustic microscopy (OR-PAM) or common photoacoustic microscopy (PAM).

In one example, both excitation and receiver beam may be combined and scanned. In this way, photoacoustic excitations may be sensed in the same area as they are generated and where they are the largest. Other arrangements may also be used, including keeping the receiver beam fixed while scanning the excitation beam or vice versa. Galvanometers, MEMS mirrors and stepper/DC motors may be used as a means of scanning the excitation beam, probe/receiver beam or both.

Figure 5A:
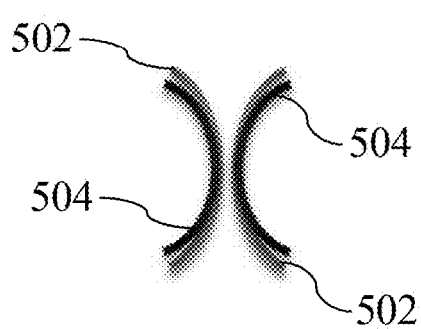
FIGS. 5A through 5D are representative drawings of the overlap between the exciter and interrogator beams on a sample.
Figure 5B:
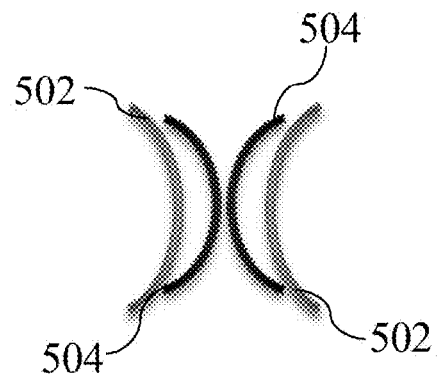
Figure 5C:
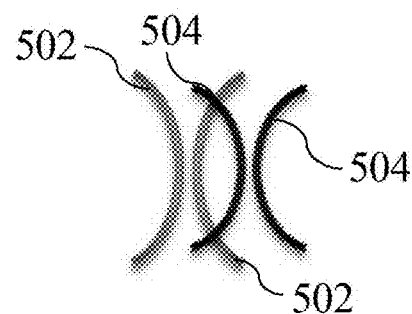
Figure 5D:
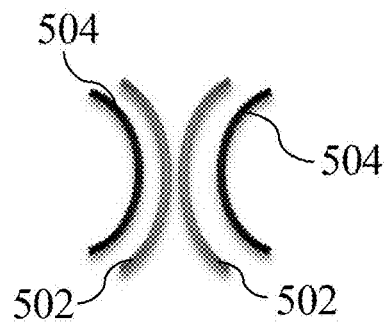

The configurations shown in FIGS. 5A, 5B, 5C, and 5D may be used to perform PARS imaging. In the depicted embodiments, lines 502, depicted with a larger radius of curvature, represent excitation beams and lines 504, depicted with a smaller radius of curvature, represent receiver beams. FIG. 5A offers a kind of confocal photoacoustic system where the excitation beam 502 and probing receive beam 504 are focused on the same spot, which can be on a micron- or sub-micron scale. In FIG. 5B, the optical resolution can be provided by the receiver beam 504, rather than the excitation beam 502. FIG. 5C shows excitation beam 502 and receiver beam 502 focused on different spots, and takes advantage of ultrasound time of flight in order to locate the excitation and receiver beams 502 and 504 at different positions. In FIG. 5D, optical resolution is provided by the excitation beam 502. Preferably, the focus of either or both of the excitation beam 502 or the detection beam 504 is less than 30 µm, less than 10 µm, less than 1 µm, or to the diffraction limit of light. A tighter focus results in a higher possible resolution and a better signal to noise ratio in the reflected beam that is detected. As used herein, the term "focus" is intended to refer to the focal zone of the beam, or the point at which the beam spot size is at the tightest size, and where the diameter of the focal zone is 30% greater than the diameter of the beam spot size. Also preferably, the excitation and detection beams 502 and 504 are focused on the same position, although there may be some spacing between the respective focuses as shown in FIG. 5C. In FIG. 5C, the beams may be focused at different locations, but preferably within 1 mm, 0.5 mm, 100 µm or within the range of the largest focus of the beam. In FIGS. 5A, 5B and 5D, the beams may be confocal, or may overlap within the focus of the beam with the largest focus. For example, in FIG. 5A, the excitation beam is larger than the detection beam, and the detection beam is directed at a location within the focus of the excitation beam. By moving the detection beam, the area within the excitation beam may be imaged. By having confocal beams, both beams may be moved to image the sample.

One or both of the beams are preferably focused below the surface of the sample. The beams may be focused, for example, using optics 36 shown in FIG. 1. Generally speaking, the beams may be effectively focused up to 1 mm below the surface of the sample. The beams may be focused at least 1 µm below the surface, or focused such that focal point of the beam is at least the distance of focal zone of the beam below the surface of the sample. It will be understood that, while both beams are preferably focused below the surface, in some embodiments either the excitation beam or the interrogation beam may be focused below the surface, with the other focused on, for example, the surface of the sample. In cases where only one beam is focused below the surface of the sample, the separation between the beams discussed previously will be a lateral separation, i.e. in the plane of the sample and orthogonal to the depth of the sample.

The excitation beam and sensing/receiver beam can be combined using dichroic mirrors, prisms, beamsplitters, polarizing beamsplitters etc. They can also be focused using different optical paths.

Figure 6:
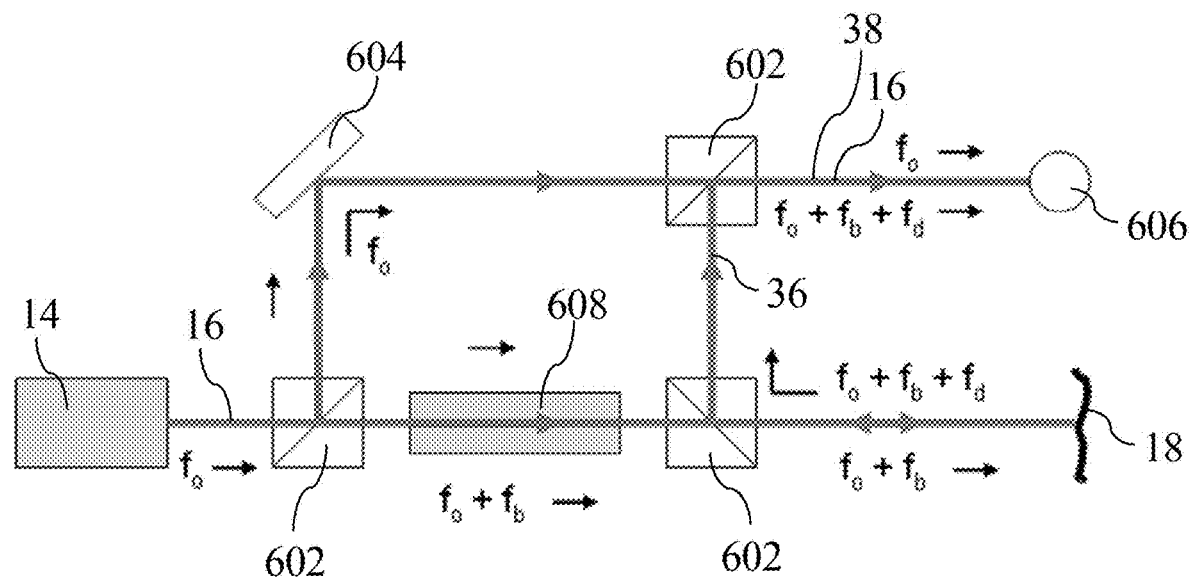
FIG. 6 is a block diagram of a sensing system involving a Doppler vibrometry configuration.

PARS can be integrated with any interferometry designs such as common path interferometer (using specially designed interferometer objective lenses), Michelson interferometer, Fizeau interferometer, Ramsey interferometer, Sagnac interferometer, Fabry-Perot interferometer and Mach-Zehnder interferometer. The basic principle is that phase (and maybe amplitude) oscillations in the probing receiver beam can be detected using interferometry and detected at AC, RF or ultrasonic frequencies using various detectors. Photoacoustic signals may also be detected using laser Doppler vibrometry configurations as shown in FIG. 6. For clarity, the excitation beam has been omitted. In this example, the detection laser 14 passes through various optical elements, including beam splitters 602 and mirror 604 in order to provide a reference optical signal and an optical signal from sample 18 that can be compared and analyzed by photodetector 606. A Bragg cell 608, or other known device, is used to frequency shift the portion of probe beam 16 that is directed to sample 18, as is known in the art.

Figure 7:
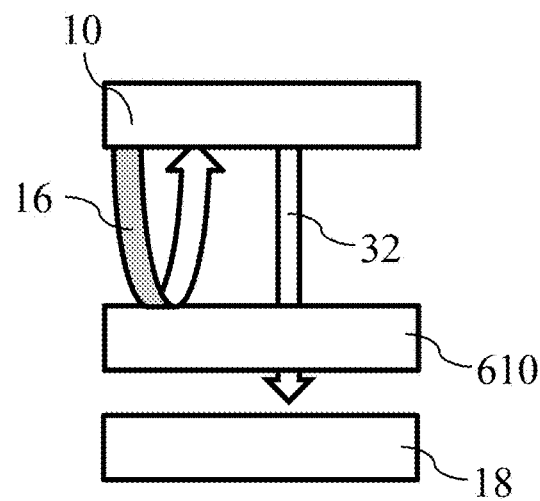
FIG. 7 is a block diagram of a sensing system using a Fabry-Perot interferometer.

Another interferometry example is shown in FIG. 7, which uses a Fabry-Perot interferometer (FPI) 610 in addition to the PARS system described above. FPI systems are all-optical detectors that offer high sensitivity and broad bandwidth important for photoacoustic imaging applications. When used with the PARS system, the FPI may result in an improved sensitivity of the system for deep imaging applications. As shown, the FPI 610 is reflective to the PARS interrogation beam 16 and visible to the PARS excitation beam 32 as shown in FIG. 7.

Figure 8:
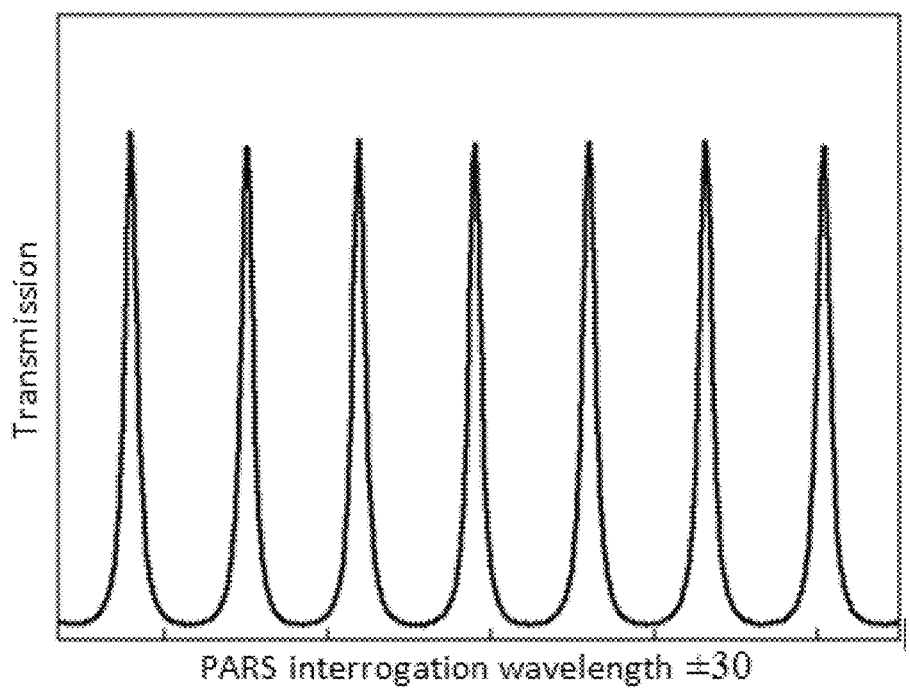
FIG. 8 is a graph of an example of the response of a Fabry-Perot interferometer.

Referring to FIG. 8, an example of the response from FPI 610 is shown, in which FPI resonant peaks are formed in the range of ±30 nm of the PARS interrogation wavelengths. For example if the PARS interrogation wavelength is 1550 nm, the range of the FPI resonant peak would be between 1520-1580 nm. The wavelength of the interrogation laser in the PARS system 10 is preferably tunable and will preferably be tuned to the sharpest slope of one the FPI resonant peaks.

Figure 9:
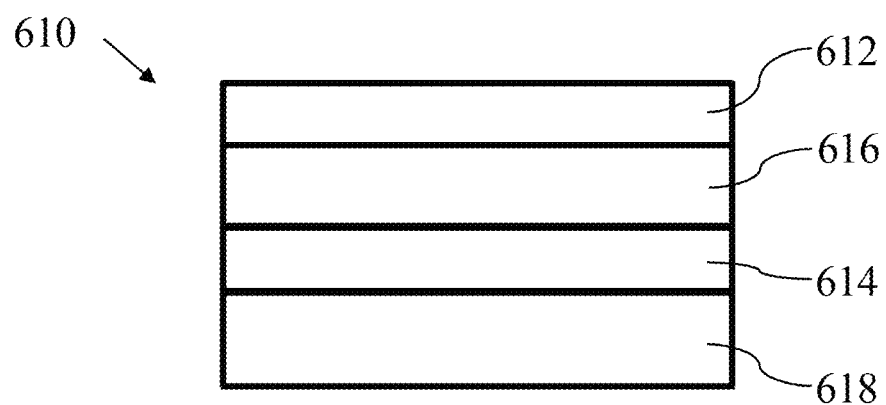
FIG. 9 is a block diagram of a Fabry-Perot interferometer.

Referring to FIG. 9, a detailed view of an example FPI 610 is shown. FPI 610 has mirrors 612 and 614 separated by a spacing material 616 and backed by a backing material 618. The photoacoustic pressure generated by the excitation beam 32 shown in FIG. 7 causes changes in the optical thickness and/or physical thickness of the spacing material 616 and/or changes in the reflectivity of the FPI mirrors. These changes will cause a temporary shift of the FPI resonant peaks to a different wavelength and as a result, changes the amount of interrogation light reflected back from the FPI to the PARS system. The amount of change in the reflected interrogation light is directly proportional to the ultrasound/photoacoustic pressure. The mirrors 612 and 614 of the FPI 610 can be fabricated using various techniques, such as glancing angle deposition (GLAD) or other suitable techniques. The spacing material 616 may be various materials, such as Parylene C, PDMS, suitable polymers, or other suitable materials. The backing material 618 may be any suitable material, such as a suitable type of glass or polymer, such as PMMA. The resonant peak of the FPI 610 may be designed to work at various wavelengths, such as between 200-2500 nm, depending on the requirements of the application. An Anti-reflection (AR) coating (not shown) can be used on one side or both side of backing material 618 to improve the light coupling into the FPI 610. It will be understood that other optical elements that are responsive to an acoustic signal may be used in place of the FPI described above, and that other optical effects other than those described above may be relied upon to enhance the detection of the ultrasonic signals in the sample.

As the PARS system 10 generally allows a user to obtain optical resolution down to sub-μm levels in a non-contact setting, adding a FPI 610 can provide acoustic resolution (i.e. greater than 30 μm) details with a penetration depth down to 7 cm. Some examples that involve the use of an FPI 610 are shown in FIGS. 10A, 10B and 10C, based on the orientation of the excitation beam 32 relative to the interrogation beam 16. As will be understood, the PARS system 10 may be used in transmission mode, such as in FIG. 10C, using independent generation and detection units. In the depicted configurations, both excitation and receiver beams may scan a sample together, one of the beams may be scanning with the other one is fixed, or both beams may be fixed. In addition, one or both excitation and receiver beams may be un-focused or loosely focused, or one or both beams may be focused.

As the PARS system takes advantage of an interferometry as explained herein, in which a reference beam is provided either by an external arm, or in a common mode path. The combination of the interferometry in the PARS system 10 as discussed previously and the FPI 610 can be used to improve the sensitivity of the photoacoustic imaging system.

In FPI-based photoacoustic imaging systems, the pressure of photoacoustic signals change the thickness of the FPI, optically and physically. These changes cause the shift of FPI resonant peaks and hence change the reflected light from the FPI. In the proposed configurations, the FPI 610 is a second interferometer that is added between the PARS system 10 and the sample 18, as shown in FIG. 7. The PARS system 10 detects surface oscillations in the FPI 610, where photoacoustic pressure physically changes the thickness of the FPI 610 and in result oscillate the FPI mirrors. The PARS system 10 as the second interferometer can pick up the oscillation of the mirrors in the FPI 610. As such, the FPI and PARS detected signal can be combined together to improve the sensitivity of photoacoustic detection. It has been found that, under this system, a detection depth of 7 cm can be reached, although resolution is generally reduced.

In another example, low coherence probe beams can also be considered for detection of photoacoustic-induced optical phase oscillations but in this case signals from the sample beam and reference beam will interfere only if the sample and reference beam paths are equal lengths plus or minus a coherence length (as in optical coherence tomography). It may also be beneficial to scan the sample or reference beam path lengths or phase for both range gating and for measuring phase oscillations over the coherent region of interference.

The reflected light may be collected by photodiodes, avalanche photodiodes, phototubes, photomultipliers, CMOS cameras, CCD cameras (including EM-CCD, intensified-CCDs, back-thinned and cooled CCDs), etc. The detected light may be amplified by an RF amplifier, lock-in amplifier, trans-impedance amplifier, or other amplifier configuration. Also different methods may be used in order to filter the excitation beam from the receiver beam before detection. PARS may use optical amplifiers to amplify detected light prior to interferometry. It may also be beneficial to demodulate via Fabry-Perot, very narrow-line optical filters, nonlinear and photorefractive crystals and/or spectral hole burning.

An alternative to scanning vibrometry is digital holographic microscopy. Methods of digital holographic microscopy may be used to read out photoacoustic-induced optical phase oscillations. In this method, a pulsed receiver beam may be used so that the sample beam and an angled reference beam interfere on an image sensor (like a CCD or CMOS camera). Using methods of Gabor or Leith-Upatneiks holography not only the amplitude can be recovered, but also the phase of the light reflected/scattered from the sample over a wide field of view. By gating when the probe beam is pulsed onto the sample relative to the excitation beam it is possible to stroboscopically reconstruct the photoacoustic signals from each point in the sample as a function of time. Alternatively, it may be possible to time-gate the camera acquisition. The excitation spot may be optically focused or focused over a wide-field. When wide-field excitation beams are used, optical-resolution can be achieved by receiving sensing optics and this resolution is anticipated to depths within a transport mean-free path in turbid media.

PARS can be used in many form factors, such as table top, handheld and endoscopy. Examples of endoscopy PARS are shown in FIGS. 11A, 11B and 11C with various arrangements of PARS excitation units 1102, PARS detection units 1104, fibre optics 1106 such as image-guide fibers, and lenses 1108 that focus the respective beams onto the sample 18. When excitation and detection units 1102 and 1104 are separated, there may be a separate fibre 1110 provided, such as a single mode fiber.

A table top and handheld PARS system may be constructed based on principles known in the art. The proposed PARS system takes advantage of optical excitation and detection which can help to dramatically reduce the footprint of the system. The footprint of previous systems has been much too large to use the system in all but body surfaces. For endoscopic applications, the footprint of the ultrasound detector must be minimized to make the imaging catheter small and flexible enough to navigate through small orifices and vessels. The piezoelectric receivers are not ideal candidates for endoscopic applications as there is trade-off between the sensitivity and the size of the receiver. On the other hand for many invasive applications sterilizable or disposable catheters and a non-contact approach are necessary. The system may also be used as PARS endoscopy system with a potential footprint the size of an optical fiber, as both excitation and PARS beam can be coupled into a single mode fiber or image guide fiber.

Image-guide fibers (miniaturized fiber bundles with as many as 100,000 or more individual micrometer-sized strands in a single optical fiber with diameters ranging from 200 µm to 2 mm) may be used to transmit both focused light spots. The excitation beam may be scanned either at the distal end or proximal end of the fiber using one of the scanning methods mentioned before. However, the receiver beam may be scanned or be fixed. The scanned spot is transmitted via the image-guide fiber 1106 to the output end. Therefore, it may be used to directly contact the sample, or re-focused using an attached miniature GRIN lens 1108. In one example, C-scan photoacoustic images were obtained from the fiber image-guides using an external ultrasound transducer to collect photoacoustic signals. Using an edge-spread and Gaussian function, a resolution of approximately 7 µm was obtained using the image-guide fiber 1106. It is believed that a higher resolution may also be obtained with appropriate improvements to the setup and equipment used.

PARS may be used to detect ultrasound signals generated from other sources including ultrasound transducers. The system may also be used as an optical vibrometer. Vibrometers have been used widely for assessing the operating condition of mechanical properties. Optical vibrometers (OV) offer various advantages over traditional vibration measurement techniques. The precise metrology of noncontact measurement, high sensitivity and accuracy are the major benefits of optical vibrometers. Most of the common optical vibrometer, including laser Doppler vibrometer (LDV) and Sagnac vibrometer are based on the optical interferometry, requiring two coherent light beams. OVs have been used for various applications including noncontact measurement of the displacement, the acceleration and the velocity of solid surfaces. The device size, cost and noise sensitivity of interferometry are limitations of the current OVs designs.

In one example, a vibrometry method based on PARS detection was used to detect by noncontact measurement of the displacement caused by ultrasound signals from a 10 MHz piezoelectric transducer. The reflected near-infrared beam from the sample is phase-modulated at the ultrasound frequency, and a beat-intensity can be detected. One example had a noise equivalent pressure of 1 KPa over 10 MHz bandwidth for real-time detection. This is improved orders of magnitude with lock-in detection. The measurement capability of the system may also be used to measure motion in high-frequency MEMS actuators and for optical detection of ultrasound.

The PARS system may be combined with other imaging modalities such as fluorescence microscopy, two-photon and confocal fluorescence microscopy, Coherent-Anti-Raman-Stokes microscopy, Raman microscopy, Optical coherence tomography, other photoacoustic and ultrasound systems, etc. This could permit imaging of the microcirculation, blood oxygenation parameter imaging, and imaging of other molecularly-specific targets simultaneously, a potentially important task that is difficult to implement with only fluorescence based microscopy methods. An example of a PARS system 10 integrated with another optical imaging system 1202 is shown in FIG. 12, where PARS 10 and the other optical imaging system 1202 are both connected to the sample 18 by a combiner 1204.

PARS may be used for A, B or C scan images for in vivo, ex vivo or phantom studies.

A multi-wavelength visible laser source may also been implemented to generate photoacoustic signals for functional or structural imaging.

PARS may be optimized in order to takes advantage of a multi-focus design for improving the depth-of-focus of 2D and 3D OR-PARS imaging. The chromatic aberration in the collimating and objective lens pair may be harnessed to refocus light from a fiber into the object so that each wavelength is focused at a slightly different depth location. Using these wavelengths simultaneously may be used to improve the depth of field and signal to noise ratio (SNR) of PARS images. During PARS imaging, depth scanning by wavelength tuning may be performed.

Polarization analyzers may be used to decompose detected light into respective polarization states. The light detected in each polarization state may provide information about ultrasound-tissue interaction.

Applications

It will be understood that the system described herein may be used in various ways, such as those purposes described in the prior art, and also may be used in other ways to take advantage of the aspects described above. A non-exhaustive list of applications is discussed below.

The system may be used for imaging angiogenesis for different pre-clinical tumor models.

The system may also be used for clinical imaging of micro- and macro-circulation and pigmented cells, which may find use for applications such as in (1) the eye, potentially augmenting or replacing fluorescein angiography; (2) imaging dermatological lesions including melanoma, basal cell carcinoma, hemangioma, psoriasis, eczema, dermatitis, imaging Mohs surgery, imaging to verify tumor margin resections; (3) peripheral vascular disease; (4) diabetic and pressure ulcers; (5) burn imaging; (6) plastic surgery and microsurgery; (7) imaging of circulating tumor cells, especially melanoma cells; (8) imaging lymph node angiogenesis; (9) imaging response to photodynamic therapies including those with vascular ablative mechanisms; (10) imaging response to chemotherapeutics including anti-angiogenic drugs; (11) imaging response to radiotherapy.

The system may be useful in estimating oxygen saturation using multi-wavelength photoacoustic excitation and PARS or PARS-etalon detection and applications including: (1) estimating venous oxygen saturation where pulse oximetry cannot be used including estimating cerebrovenous oxygen saturation and central venous oxygen saturation. This could potentially replace catheterization procedures which can be risky, especially in small children and infants.

Oxygen flux and oxygen consumption may also be estimated by using OR-PARS or PARS-etalon imaging to estimate oxygen saturation, and an auxiliary method to estimate blood flow in vessels flowing into and out of a region of tissue.

The system may also have some gastroenerological applications, such as imaging vascular beds and depth of invasion in Barrett's esophagus and colorectal cancers. Depth of invasion is key to prognoisis and metabolic potential. Gastroenterological applications may be combined or piggybacked off of a clinical endoscope and the miniaturized PARS/PARS-etalon system may be designed either as a standalone endoscope or fit within the accessory channel of a clinical endoscope.

The system may have some surgical applications, such as functional imaging during brain surgery, use for assessment of internal bleeding and cauterization verification, imaging perfusion sufficiency of organs and organ transplants, imaging angiogenesis around islet transplants, imaging of skingrafts, imaging of tissue scaffolds and biomaterials to evaluate vascularization and immune rejection, imaging to aid microsurgery, guidance to avoid cutting critical blood vessels and nerves.

Other examples of applications may include PARS/PARS-etalon imaging of contrast agents in clinical or preclinical applications; identification of sentinel lymph nodes; non- or minimally-invasive identification of tumors in lymph nodes; imaging of genetically-encoded reporters such as tyrosinase, chromoproteins, fluorescent proteins for preclinical or clinical molecular imaging applications; imaging actively or passively targeted optically absorbing nanoparticles for molecular imaging; and imaging of blood clots and potentially staging the age of the clots.

PARS Mechanism

There will now be given a more detailed discussion of the PARS modulation mechanisms, and comparison with experiment.

The total intensity of light incident on the photodiode is given as the ensemble average of the squared magnitude of the sample and reference beam electric fields (taking constant factors as unity for convenience):

$$I_{PD} = \langle |E_S + E_R|^2 \rangle$$

The power of light reflected from the surface of the sample then routed to the photodiode is estimated as $0.9^2 R_I I_0$ where $I_0$ is the incident intensity from the source, and $R_I$ is the intensity reflection coefficient at the air-sample interface and a factor of 0.9 is included for each pass through a 10:90 beamsplitter. Likewise the reference beam power is estimated as $I_R = \langle |E_R|^2 \rangle = 0.1^2 \eta_{VNDF}^2 I_0$ where $\eta_{VNDF}$ is the transmissivity of the variable neutral density filter (VNDF).

Possible mechanisms include a pressure-induced refractive-index modulation, thermally-induced refractive index modulation, surface oscillations, and scatterer position modulation due to confined thermal expansion. Each mechanism will be discussed below.

Pressure-Induced Refractive-Index Modulation

Refractive index changes due to temperature and pressure rises may in turn affect the scattering of light. We first consider pressure changes. Local initial pressures may be calculated as very large when optical focusing and thermal confinement conditions are applied: The initial pressure is given as $P_0 = \Gamma \Phi \mu_a$ where $\Gamma$ is the Gruneissen parameter, Assuming 532 nm light is focused to a micron scale spot size with a focal fluence, $\Phi$, of 500 mJ/cm² and that this light is absorbed by oxygenated blood which has an estimated optical absorption coefficient $\mu_a$ of $0.0054 \times 43876 = 236.9$ cm$^{-1}$ (calculated at this wavelength assuming a hemoglobin concentration of 150 g/L and assuming no optical absorption saturation) the absorbed energy produces a transient temperature rise on a micro-scale as high as 30K. Using the above parameter estimates, we calculate an initial pressure as high as 118.5 MPa for unity Grueneisen parameter.

The optical refractive index experiences a perturbation to pressure variations estimated as $$n(r,t) = n_0(1 + \eta n_0^2 P(r,t)/2\rho v_a^2)$$

where $n_0$ is the unperturbed optical refractive index, $\eta$ is the elasto-optic coefficient (~0.32 for water), $P(r, t)$ is the pressure field, $\rho$ is mass density and $v_a$ is the speed of sound. The accumulated phase shift of light passing through a zone of enhanced pressure can be calculated by Raman Nath diffraction theory and will depend on the direction of the sound and the direction of the light as well as the pressure field inhomogeneity. For a light beam incident on a plane pressure wave where both the light and sound beams are parallel the accumulated phase shift should be zero and are rather maximum when sound fields create effective diffraction gratings orthogonal to the light propagation. Rather than calculate the phase shifts of transmitted light we are more interested in the light reflected from a refractive index mismatch. With 100 MPa initial pressure a refractive index step of $\Delta n \sim 0.019$ is predicted in the confined excitation volume, which is a 1.4% change. This results in an optical reflection coefficient of 0.7% which is very measurable.

This mechanism will contribute to both amplitude and phase variations in the probe beam.

The electric field back-reflected from the sample and incident on the photodiode is modelled as having two components, AC and DC terms:

$$E_S = E_{DC,S} + E_{AC,S}$$

Here $E_{DC,S} = \sqrt{0.9^2 R_I I_0}$ is the electric field magnitude of light reflected from the sample surface and $E_{AC,S} = \sqrt{0.9^2 I_0 T_I^2 e^{-2\mu_{eff} d} R_{I,P}}$ is the electric field amplitude of light reflected from the excitation volume beneath the surface due to a transient pressure induced optical index step. $T_I$ is the transmission intensity coefficient at the air-tissue interface. Here both ballistic and scattered photons are accounted for as reflecting from the index step hence $e^{-2\mu_{eff}d}$ is the effective light attenuation over depth d in a scattering medium with effective attenuation coefficient $\mu_{eff}$. The factor of 2 accounts for a round trip. The fraction of light modulated $F_p$ is calculated as the AC terms from the expansion of $I_{PD}= \langle |E_S+E_R|^2 \rangle$ divided by the DC terms. If the modulated light scattered from the excitation volume contains multiply scattered photons as we have assumed, then because phases of the AC component of the sample are effectively randomized the ensemble average of products of $E_{AC,S}$ with reference beam $E_R$ or $E_{DC,S}$ will be zero, leaving the fraction of light modulated as:

$$F_P = \frac{\langle |E_{AC,S}|^2 \rangle}{\langle |E_R|^2 \rangle + \langle |E_{DC,S}|^2 \rangle}$$

Thermally-Induced Refractive Index Modulation

Thermal effects also change refractive indices. Given the volumetric thermal expansion coefficient of water is $a_v=207\times10^{-6}K^{-1}$ at 20° C. and it's refractive index is 1.33, the refractive index would change ~0.01%/° C., hence ~0.3% with a 30° C. temperature rise, which is small but potentially noticeable as a source of scattering modulation. However, this effect would only be applicable locally at the heating zone. Thermal cooling will occur on a scale of microseconds-to-milliseconds after laser-induced heating.

Surface Oscillations

The above mechanisms point to significant sources of scattering position or scattering cross-section modulation that could be readily measurable when the probe beam is focused to sense the confined excitation volume. However, these large local signals are not the only potential source of signal modulation. Acoustic signals propagating to the surface could also result in phase modulation of the reflected light. Sound pressures decay as 1/r due to diffractive losses so pressure signals can be significantly weaker away from the confined heating region compared to at their source. For example, assuming an isotropic spherical heating region of diameter 5 microns (e.g. an isolated red blood cell) the sound pressure level at the boundary of the sphere is estimated as ~100 MPa but 1 mm away this is predicted as only 2.5/1000*100 MPa. ~0.25 MPa. Surface pressure modulation can cause surface oscillations and the reflection of the interrogation beam from this oscillating surface can be a source of detected signal. For a local plane wave at the tissue surface with peak pressure p the particle velocity is estimated as $$v_p = \frac{p}{z}$$

where Z is the characteristic acoustic impedance. For a sinusoidal pressure field the particle/surface displacements are thus $\Delta z \sim v_p/\omega_a$ which is a couple of nm for 10 MHz ultrasound with 0.25 MPa amplitude. This is a fraction of a wavelength but still a significant source of phase modulation considering the surface reflectivity may be high and will return significant amounts of incident probe-beam light back to the detector. Notice, however, that this surface modulation has a $1/\omega_a$ dependence hence there is an inherent low-pass filtering effect that could be rejecting high-frequency components. Nevertheless such signals are readily measurable by our system, as evidenced by when we position the probe beam away from the excitation beam and can still form images when we scan the excitation spot.

If we assume that only surface oscillations are considered, the electric field phasor from the sample surface is modelled as $E_S=E_{S0} \cos(kz \cos(\omega_a t)) \sim E_{S0}(J_0(kz)+J_1(kz)e^{j\omega_a t}+\ldots)$ for a continuous wave modulation at acoustic angular frequency $\omega_a$. Here $E_{S0}=\sqrt{0.9^2 R_f P_0}$. In this case we do not need to worry about light propagating into the sample, and the fraction of light modulated by surface oscillations is estimated as:

$$F_S = \frac{2\langle |E_{DC,S} E_{AC,S}|\rangle + 2\langle |E_R E_{AC,S}|\rangle}{\langle |E_{DC,S}|^2\rangle + \langle |E_{AC,S}|^2\rangle + \langle |E_R|^2\rangle + 2\langle |E_R E_{DC,S}|\rangle} = \frac{2E_{S0}^2 J_0(kz) J_1(kz) + 2E_{S0} E_R J_1(kz)}{E_{S0}^2 J_0^2(kz) + E_{S0}^2 J_1^2(kz) + E_R^2 + 2E_{S0} E_R J_0(kz)}$$

Scatterer Position Modulation Due to Confined Thermal Expansion

The volumetric thermal expansion coefficient of water is given as $a_v=207\times10^{-6}K^{-1}$ at 20° C. Assuming a transient temperature rise on a micro-scale as high as 30K as calculated above, a volumetric expansion $$\frac{\Delta V}{V} = 207 \times 10^{-6} K^{-1} \times 30K = 6.21 \times 10^{-3}$$

is predicted. For a given temperature rise, the smaller the heated volume the larger the expansion. Now if the light is absorbed from a 3-micron spot size with a volume modelled as the 1/e penetration depth times the cross-sectional illumination area the isotropic particle motion is modelled as $$\left(6.21 \times 10^{-3} \times \pi(r)^2 \times DOF_{ex}\right)^{\frac{1}{3}} = 1 \ \mu m$$

which is larger than the wavelength and a very large modulation, where r is the radius of the excitation beam spot size at focus and $DOF_{ex}$ is the depth of field of excitation beam calculated using Gaussian beam parameters, ~27 μm.

EXPERIMENTAL RESULTS

Experimental Setup

There will now be given an example of experimental methods and setup that was used to test the principles discussed herein. A modified version of polarization sensitive Michelson interferometry has been employed to remotely record the large local initial pressures from chromophores and without appreciable acoustic loses. The experimental setup of the optical-resolution photoacoustic remote sensing (OR-PARS) microscopy system is depicted in FIG. 20. A multi-wavelength visible laser source using stimulated Raman scattering (SRS) has been implemented to generate photoacoustic signals. Briefly, a 1 ns pulse width, frequency doubled ytterbium-doped fiber laser (IPG Photonics Inc.) with a pulse repetition rate (PRR) of 40 kHz was coupled using a fiber launch system (MBT621D/M, Thorlabs Inc.) into a 3 m polarization-maintaining single-mode fiber (PM-SMF) (HB-450, Fibercore Inc., UK) to generate SRS peaks at 543, 560, 590, and 600 nm and pulse energies up to 500 nJ. The system has been optimized in order to takes advantage of a multi-focus OR-PAM for improving the depth-of-focus of 2D and 3D OR-PARS imaging. FIG. 20 shows a tunable pulsed laser source at 2202, made up of pulsed laser 12, and having polarization maintaining single mode fiber 2204, frequency doubler 2206, collimator lenses 2208, and polarization maintaining nonlinear fibre 2210. Collimator lenses 2208 and the second polarization maintaining nonlinear fibre 2210 make up the SRS peak generation region 2212. After exiting the tunable pulsed laser source 2202, the beam may encounter an optional band pass filter wheel 2214 before being reflected by mirror 2216. Dual beam combiner 2218 passes the beams to galvanometer scanning mirror 2220, through Objective lens 58, and to sample 18. Galvanometer scanning mirror 2220 is controlled by controller and driver 2222, which receives instructions from function generator 2224. Detection laser 14 may be a continuous wave laser, having single mode fiber 2226 followed by collimator lens 2208. The beam from detection laser 14 is then passed through polarized beam splitter 44. A portion of the split beam passes through lens 42 to photodiode 2228, through transimpedance amplifier 2230, low-noise amplifier 2232, band pass filter 2234, to analog to digital convertor 2236, providing input for controlling the galvanometer scanning mirror 2220, as will be understood by persons skilled in the art. The other portion of the beam is directed through quarter wave plate 56, through 10:90 beam splitter 2238, where the beam is either passed through variable neutral density filter 2240 to mirror 2242 to provide reference beam 2244, or through band pass filter 2246 to combine with the beam from the pulsed laser 12 at the dual beam combiner 2218.

The chromatic aberration in the collimating and objective lens pair was harnessed to refocus light from a fiber into the object so that each wavelength is focused at a slightly different depth location. Using these wavelengths simultaneously was previously shown to improve the depth of field and SNR for structural imaging of microvasculature with OR-PAM. The differences between the multi-focus and single wavelength in vivo images will be discussed below.

The output of the PM-SMF was collimated (F280APC-A, Thorlabs Inc.) and combined using a dichroic beam combiner (DBC) with the receiver arm of the system. For the receiver arm a continuous wavelength (CW) C-band laser with 100-kHz linewidth (TLK-L1550R, Thorlabs Inc., New Jersey) was used.

The light at the laser aperture was coupled to a single mode fiber and collimated. The randomly polarized collimated interrogation beam was passed through a polarized beam splitter (VBA05-1550, Thorlabs Inc., New Jersey) to be linearly polarized and a λ/4 zero order wave plate (Thoriabs Inc., New Jersey) to be circularly polarized. The circularly polarized light then passes through a beam splitter (BS) with 10:90 ratio. A variable neutral density filter (NDF) and then a mirror has been placed at the 10% output of the BS in order to provide the optimized reference power of the interferometry. The beam at the 90% output of the BS has been combined by the excitation arm and then scanned across the samples via a 2D galvanometer scanning mirror system (GVS012/M, Thorlabs Inc.). The scanning mirrors were driven by a two-channel function generator. The scanning light was then focused tightly using an objective lens (M Plan Apo NIR 20X, Mitutoyo, Japan). The reflected light back through the wave-plate creating 90° polarization which then reflects at the polarizing beam-splitter in order to guide the maximum possible intensity of reflected light to a 150 MHz-bandwidth InGaAs photodiode (PDA10CF, Thorlabs Inc., New Jersey). A band pass filter (BPS) has been placed on the detection arm to reject the excitation bean. An objective lens (518125, LEICA, Germany) was used in front of the photodiode (not shown in the figure) in order to refocus all possible reflected interrogation light to the small photodiode aperture. The output of the photodiode was amplified using an RF amplifier (Olympus 5900PR) with a band pass filter (1 MHz-20 MHz) and 26 dB gain and then digitized using a 4-channel PCI digitizer (Gage card) at a sampling rate of 200 MSamples/s. To form images, we project the maximum amplitude of each A-scan as a pixel in a C-scan en-face image, similar to previous PAM approaches. Since there are no optical components between the objective lens and the sample (unlike other reflection mode photoacoustic systems), therefore optical aberrations can be minimized. Interferometry model for PARS microscopy has been discussed in the supplementary information section.

FIG. 22 shows two other examples of interferometry designs, having one of two continuous wave lasers 2404 and 2406. Setup 1, shown at 2410, uses common path interferometry. Continuous wave laser 2404 provides a beam through polarized beam splitter 44, where it is split either toward photodiode 46, or through quarter wave plate 56 and then to beam combiner unit 30. Setup 2, shown at 2412, uses Michelson interferometry. Continuous wave laser 2406 provides a beam to 10:90 beam splitter 2238, where it is sent to another photodiode 46, neutral density filter 2408, or to beam combiner unit 30. In both setups shown, pulse laser 12 provides an additional beam to polarization maintaining single mode fiber 2402, lens system 42, and then to beam combiner unit 30. From beam combiner unit 30, the beam then passes through objective lens 58 and encounters sample 18.

In a Michelson interferometry, as shown in FIG. 22, a non-polarized beam splitter 2238 with 10:90 ratio may be used. A variable neutral density filter (NDF) 2408 on a 3-axis stage may be placed at the 10% output of the beam splitter 2238 in order to provide the optimized reference power. Like the configuration shown in FIG. 20, the interrogation beam may be combined with the excitation beam and scanned through an objective lens 58 on the sample 18. For both configurations, an objective lens (518125, LEICA, Germany, not shown) may be used in front of the photodiode 46 in order to refocus all possible reflected interrogation light to the small photodiode element. The output of the photodiode 46 may be amplified (Olympus 5900PR) and digitized using a 4-channel PCI digitizer (Gage card) at a sampling rate of 200 MSamples/s.

Results and Discussion

FIG. 13A shows PARS imaging of carbon fiber networks using ~1 nJ excitation pulse energy and 6 mW interrogation power. SNR (defined as average of signal over the standard deviation of the noise) was quantified as 45±3 dB. FIG. 13B shows FWHM due to fitting individual carbon fiber (with ~6 µm diameter) signal amplitude to a Gaussian function. FIG. 13C shows the resolution study using a knife edge spread function. The lateral resolution of the system has been measured as ~2.5±1 µm. FIG. 13D compares the images of reflection mode PARS and a transmission mode OR-PAM using a 10 MHz unfocused transducer (Olympus, V312-SM), The transmission mode OR-PAM setup was not capable of imaging with 1 nJ pulse energy. FIG. 13D was formed using 50 nJ pulse energy and images were recorded simultaneously.

In order to validate that the ultrasound signals can be detected directly, the system shown in FIG. 13D was used to analyze a sample 18, which includes a PARS system 10 and an ultrasound transducer 1302 to directly detect the ultrasound signals generated by the ultrasound transducer 1302. The PARS system 10 is also capable of detecting noncontact measurement of the displacement caused by ultrasound signals from an unfocused piezoelectric transducer (Olympus, A312-10 MHz/0.25"). A small amount of water was used at the top of the transducer 1302 and the transducer was driven by a sine wave from a function generator at 10 MHz. The proposed system has a noise equivalent pressure of ~1 KPa.

Figure 14A:
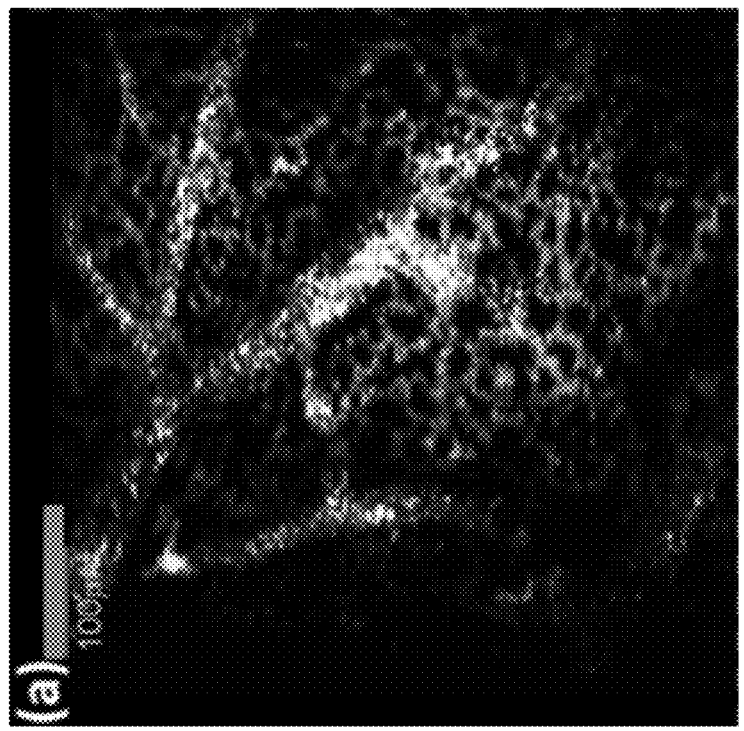
Figure 14B:
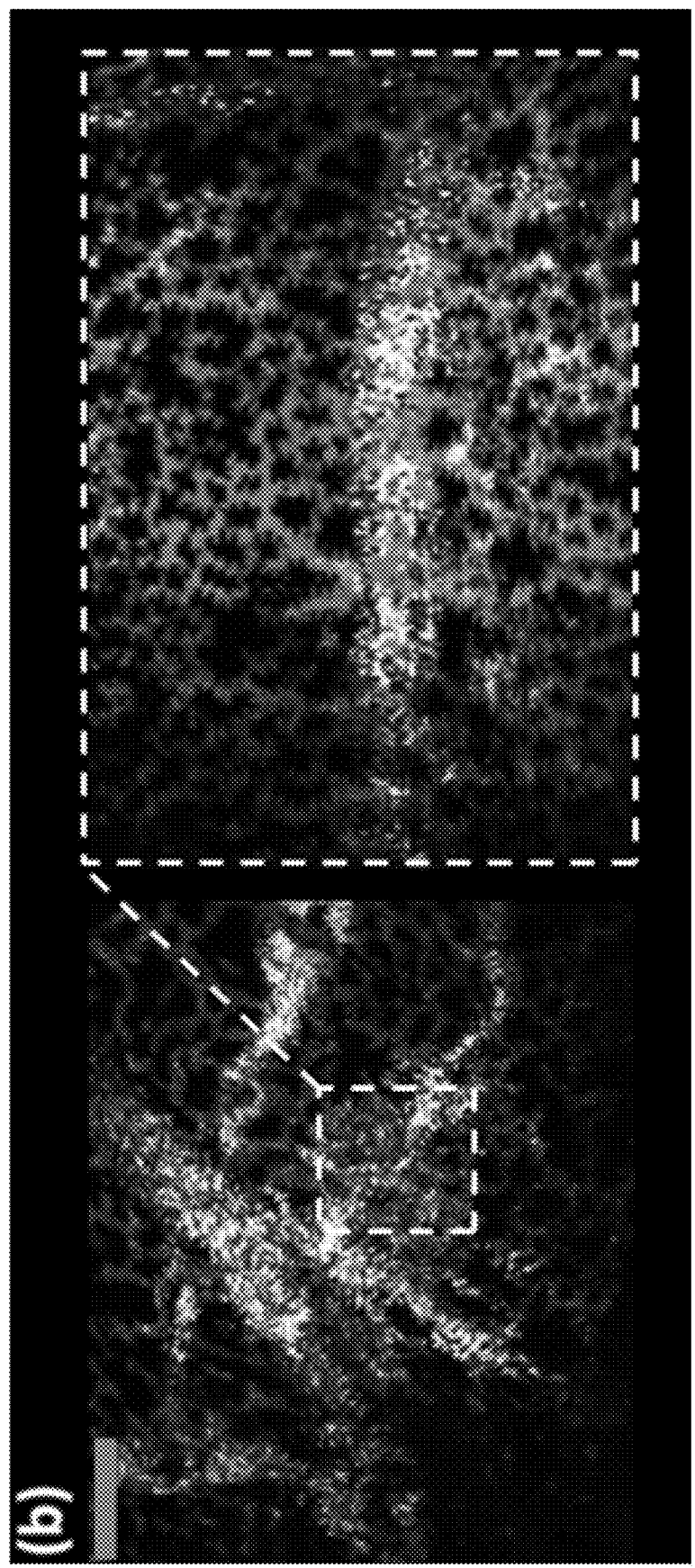
Figure 14C:
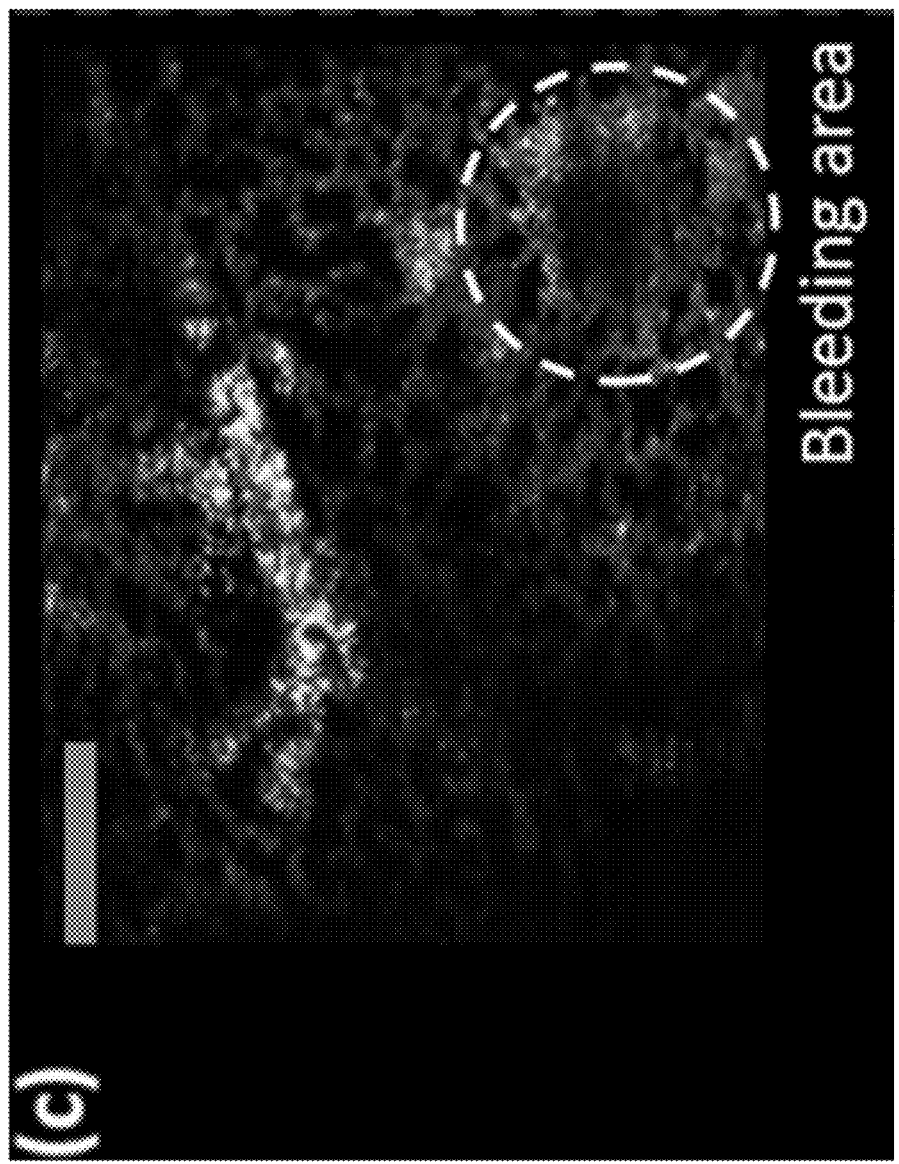
Figure 14D:
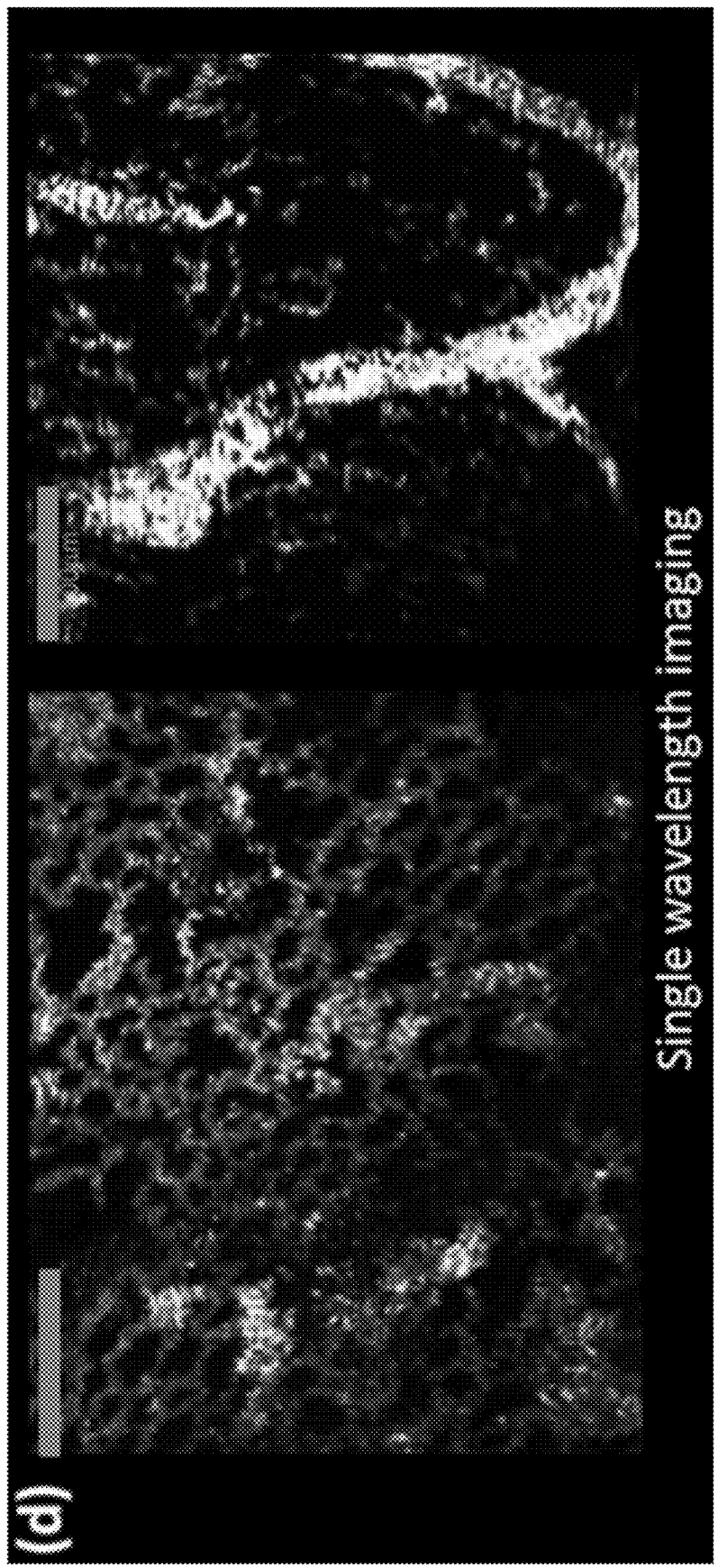

FIGS. 14A, 14B, 14C, and 14D show in vivo images of CAM-membrane of 5-day chicken embryos. FIG. 14A shows multi focus PARS images revealing both capillary beds and bigger blood vessels. In the chicken embryo model bigger blood vessels usually are located deeper than capillaries. In order to see both deep- and shallow vessels simultaneously the multi-focus design is optimized to extend the depth-of-field to ~250 µm. FIG. 14B shows a zoomed-in image of both capillary beds and bigger blood vessels. FIG. 14C shows that PARS is capable of indicating the bleeding area in the tissue. The bleeding area caused intentionally by using very high pulse energy. FIG. 14D shows PARS images acquired with a single wavelength (532 nm) rather than multiple wavelengths. With a single wavelength, depth-of-focus is limited to ~30 µm, rather than 250 µm with the multi-focus approach. Hence single-wavelength excitation is better-suited for depth-sectioning. This is evident in FIG. 14D, where top capillary beds are seen but not deeper large vessels. When we scan deeper with single wavelength excitation we see larger deep vessels but not superficial capillary beds. A comparison between images in FIGS. 14A and 14B, with FIG. 14D indicate that multi-focus design helps to improve the SNR of maximum amplitude C-scan images and improve the depth of field of the system compare to a single wavelength imaging. All the images shown herein are raw data and no major image processing steps are applied.

The PARS system is capable of imaging when both beams are scanning together, or when the interrogation beam is fixed and excitation beam is scanning. The field of view will be limited in this case as the generated photoacoustic signals will experience more attention if they are located far from the fixed interrogation beam.

FIG. 15 is a chart of the measured photoacoustic signals from various dye concentrations. FIG. 16 shows the photoacoustic signal (V) vs. energy of the excitation laser (nJ) on the sample when the interrogation power is fixed at 8 mW. It shows a linear response as expected. FIG. 17 shows the photoacoustic signal vs. interrogation power (mW) on the sample when excitation energy is fixed at 60 nJ. It is shown that after ~11 mW the photodiode goes to its saturation region.

FIG. 18A depicts the PARS frequency response and FIG. 18B depicts the PARS photoacoustic time domain signal of an individual carbon fiber. Referring to FIGS. 18C and 18D, the charts represent time domain photoacoustic signal of a single carbon fiber with ~7 µm diameter when the excitation and interrogation beams are separated by ~120 and 330 µm, respectively. The −3 dB bandwidth was measured as ~20 MHZ by imaging carbon fiber network as shown in FIG. 13A. The band pass response was expected as the RF amplifier was set to a band pass filter (1 MHz-20 MHz). The axial resolution of the system is measured ~75 µm. In FIG. 18b, both excitation and interrogation beam have been co-aligned in the x and y direction and co-focused together in the z direction. Therefore, the photoacoustic signal starts at the time zero. However in FIGS. 18C and 18D, a time shift has been measured as the excitation and interrogation beams are separated by ~120 and 330 µm, respectively. The results clearly show the ultrasound time of flight variation by changing the location of detection spot.

FIGS. 19A, 19B, 19C, and 19D depict in vivo PARS images of a mouse ear, and FIGS. 23A, 23B, 23C, and 24 show in vivo PARS images of a 100 g rat's ear. In all in vivo images pulse energy ~20-80 nJ was used and the interrogation power was fixed to 6 mW. The selection of excitation and interrogation lasers will be discussed below.

Unlike OCT, PARS takes advantage of a high coherence interrogation beam in the low coherence interferometry, backscattered light is detected from a selected depth (via coherence gating). However in PARS high-coherence method signals from all depths can be detected. The depth of images shown in FIGS. 14A, 14B, 14C, and 14D was measured ~1.5 mm. This may be reduced to ~1 mm in media with higher turbidity where focusing is limited to a transport mean-free path. Aside from depth considerations, high-coherence interrogation beams may offer improved signal contrast and signal-to-noise compared to low-coherence lasers. A stochastic model is discussed in the supplementary information section.

FIG. 21 shows the measured signal from an unfocused transducer at different lateral distances. The depth of focus of the detection beam on the sample is measured as ~50 µm. Therefore, the focus spot diameter of the detection beam on the sample is measured as ~7 µm. We also measured the photoacoustic signal generated by different dye concentrations to prove the concept of optical absorption for photoacoustic imaging. It is shown in FIG. 15 that that the sample with higher absorption coefficient provides bigger photoacoustic signals as expected.

Discussion

In summary the results above showed that: (1) the PARS signal strength is proportional to optical absorption; (2) the PARS signal strength increases linearly with both signal- and reference beam intensities; (3) the PARS signals are largest at the optical focal zone (4) the detected signals are indeed photoacoustic signals; (5) signal maximization occurs when excitation and detection beams are confocal; (5) long-coherence of the probe beam is important for signal-to-noise; (6) PARS signal detection is possible at superficial depths in multiply scattering tissue; (7) lateral resolution will principally be determined by the excitation spot size; (8) axial resolution will principally be determined by detection system bandwidth; and (9) depth sectioning can be achieved with high numerical aperture objectives while extended depth-of-field can be achieved by harnessing chromatic aberration with multi-spectral excitation source.

As will be understood, the high sensitivity and the fine resolution of the proposed system offer performance comparable to other in vivo optical resolution photoacoustic microscopy systems but with much higher signal to noise ratio and in a non-contact reflection mode suitable for many clinical and pre-clinical applications. In this method a multi-wavelength fiber laser in the visible range has been used in multi focus form to generate photoacoustic signals and the acoustic signatures have been interrogated using a long-coherence length probe beam co-focused and co-aligned and co-scanned with the excitation spots.

Selecting an excitation laser may involve the following considerations. First, it should be capable of producing suitable conditions of stress- and thermal-confinement that both heat- and stress-build up during the course of a laser pulse before the energy can propagate away in the form of thermal diffusion or acoustic propagation. Stress confinement is the most stringent of the two criteria. For example, for 2 µm focused excitation spot, laser pulses should be preferably shorter than 2 µm/1500 m/s=1.3 ns, which would require a laser with pulse widths of a nanosecond or shorter. Second, the repetition rate of the laser will determine the imaging frame rate: the faster the repetition rate the higher. However, the repetition rate is preferably not so high that signals from previous pukes overlap in time with subsequent pulses. Given that the imaging depth is not likely to be more than about a transport mean-free path (~1 min in tissue) the maximum pulse-repetition rate is preferably on the order of 1 MHz, Pulse energy should be such that ANSI limits are met at the tissue surface, requiring sub-µJ levels of pulse energy. Finally the wavelength of the excitation source should preferably be tunable for multi-spectral imaging purposes. These considerations are similar to those for OR-PAM and it is known that fiber lasers can be a good choice. In one example, a frequency doubled Ytterbium-doped fiber laser was used to achieve tenability inject µJ-scale ns-pulses at 532-nm into a length of nonlinear fiber to generate Stimulated Raman Scattering peaks. A range of wavelengths may be generated using this technique with enough pulse energy for OR-PAM. Few other sources are capable of meeting this range of requirements.

The selection of the interrogation laser is also important. As described above, the linewidth of the probe laser should be significantly smaller than the acoustic frequencies to be detected otherwise significant noise power from the laser source could leach into the passband of the system and degrade SNR. In one example, a laser was used with a 100 KHz linewidth, which is significantly smaller than the MHz-level frequencies to be detected. The laser is preferably tunable in wavelength and power, although wavelength tuning is not critical. A wavelength of 1550 nm may be used with a 532 nm excitation light because it is spectrally different (important so that optical filters can prevent excitation light from hitting the detector) and because it is a key band in optical communications where a plethora of components are available. Water absorption at this wavelength is higher than desirable: the 1/e penetration depth is a few mm. Other wavelength bands could also be used.

In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The scope of the following claims should not be limited by the preferred embodiments set forth in the examples above and in the drawings, but should be given the broadest interpretation consistent with the description as a whole.

The invention claimed is:

1. A system for visualizing details in a sample, comprising:
one or more light sources configured to generate:
a first beam configured to generate signals in a sample at a first location, and
a second beam incident on the sample at the first location, a portion of the second beam returning from the sample that is indicative of the generated signals;
an optical system configured to focus at least one of the first beam or the second beam below a surface of the sample; and
a detector configured to detect the returning portion of the second beam,
wherein the system does not contact the sample.

2. The system of claim 1, wherein the one or more light sources include one or more lasers.

3. The system of claim 1, wherein the first beam is pulsed or intensity-modulated.

4. The system of claim 1, wherein the second beam is pulsed, intensity-modulated, or continuous.

5. The system of claim 1, wherein the generated signals are ultrasonic and/or photoacoustic signals.

6. The system of claim 1, wherein the generated signals are thermal signals.

7. The system of claim 1, wherein the optical system is configured to:
focus the first beam at a first focal point that is below the surface of the sample, and
focus the second beam at a second focal point that is below the surface of the sample.

8. The system of claim 1, further comprising a processor configured to calculate an image based on the returned portion of the second beam.

9. The system of claim 8, wherein the processor is configured to analyze the generated signals as a function of time.

10. The system of claim 8, wherein the processor is configured to determine a maximum amplitude for the generated signals.

11. The system of claim 8, wherein the image is a maximum amplitude projection (MAP) image.

12. The system of claim 1, wherein the system is used in one or more of the following applications:
imaging of blood oxygen saturation;
imaging of tumor hypoxia;
imaging of wound healing, burn diagnostics, or surgery;
imaging of microcirculation;
blood oxygenation parameter imaging;
estimating blood flow in vessels flowing into and out of a region of tissue;
imaging of molecularly-specific targets;
imaging angiogenesis for pre-clinical tumor models;
clinical imaging of micro- and macro-circulation and pigmented cells;
imaging of the eye;
augmenting or replacing fluorescein angiography;
imaging dermatological lesions;
imaging melanoma;
imaging basal cell carcinoma;
imaging hemangioma;
imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;

imaging melanoma cells;
imaging lymph node angiogenesis;
imaging response to photodynamic therapies;
imaging response to photodynamic therapies having vascular ablative mechanisms;
imaging response to chemotherapeutics;
imaging response to anti-angiogenic drugs;
imaging response to radiotherapy;
estimating oxygen saturation using multi-wavelength photoacoustic excitation;
estimating venous oxygen saturation where pulse oximetry cannot be used;
estimating cerebrovenous oxygen saturation and/or central venous oxygen saturation;
estimating oxygen flux and/or oxygen consumption;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;
imaging of blood clots; or
staging an age of blood clots.

13. A system, comprising:
one or more light sources configured to:
generate signals in the sample at a first location using a first beam, the first beam being focused below a surface of a sample, and
interrogate the sample with a second beam directed toward the first location of the sample, the second beam being focused below the surface of the sample; and
a detector configured to detect a portion of the second beam returning from the sample,
wherein the system does not contact the sample.

14. The system of claim 13, further comprising a processor configured to form an image based on the returned portion of the second beam.

15. The system of claim 14, wherein the processor is configured to determine a maximum amplitude of the generated signals and project the maximum amplitude as a pixel to form the image.

16. An endoscopic device including the system of claim 13.

17. The endoscopic device of claim 16, including a cable having a first end and a second end, wherein the one or more light sources and the detector are provided at the first end.

18. The system of claim 13, wherein the system is used in one or more of the following applications:
imaging of blood oxygen saturation;
imaging of tumor hypoxia;
imaging of wound healing, burn diagnostics, or surgery;
imaging of microcirculation;
blood oxygenation parameter imaging;
estimating blood flow in vessels flowing into and out of a region of tissue;
imaging of molecularly-specific targets;
imaging angiogenesis for pre-clinical tumor models;
clinical imaging of micro- and macro-circulation and pigmented cells;
imaging of the eye;
augmenting or replacing fluorescein angiography;
imaging dermatological lesions;
imaging melanoma;
imaging basal cell carcinoma;
imaging hemangioma;
imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;
imaging melanoma cells;
imaging lymph node angiogenesis;
imaging response to photodynamic therapies;
imaging response to photodynamic therapies having vascular ablative mechanisms;
imaging response to chemotherapeutics;
imaging response to anti-angiogenic drugs;
imaging response to radiotherapy;
estimating oxygen saturation using multi-wavelength photoacoustic excitation;
estimating venous oxygen saturation where pulse oximetry cannot be used;
estimating cerebrovenous oxygen saturation and/or central venous oxygen saturation;
estimating oxygen flux and/or oxygen consumption;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;

imaging of blood clots; or
staging an age of blood clots.

19. A method of visualizing details in a sample, the method comprising the steps of:
   receiving, via one or more reflected beams, one or more photoacoustic remote sensing (PARS) signals;
   determining a maximum amplitude of the received one or more PARS signals; and
   projecting the maximum amplitude as a pixel to form an image visualizing details in a sample,
   wherein the method does not use a transducer.

20. The method of claim 19, wherein the PARS signals are collected by:
   generating signals in the sample at an excitation location using an excitation beam of light, the excitation beam being focused below a surface of the sample; and
   interrogating the sample with an interrogation beam of light directed toward the excitation location of the sample, the interrogation beam being focused below the surface of the sample, wherein the one or more reflected beams include a portion of the interrogation beam returning from the sample.

* * * * *